(12) United States Patent
Bredif et al.

(10) Patent No.: US 11,892,447 B2
(45) Date of Patent: Feb. 6, 2024

(54) METHOD FOR EVALUATING THE EFFECTS OF DEHYDRATION ON CHILDREN'S SKIN

(71) Applicant: Laboratoires Expanscience, Paris la Défense (FR)

(72) Inventors: Stephanie Bredif, Croisilles (FR); Caroline Baudouin, Rambouillet (FR)

(73) Assignee: Laboratoires Expanscience, Paris la Defense (FR)

( * ) Notice: Subject to any disclaimer, the term of this patent is extended or adjusted under 35 U.S.C. 154(b) by 111 days.

(21) Appl. No.: 16/062,488

(22) PCT Filed: Dec. 16, 2016

(86) PCT No.: PCT/EP2016/081562
§ 371 (c)(1),
(2) Date: Dec. 17, 2018

(87) PCT Pub. No.: WO2017/103195
PCT Pub. Date: Jun. 22, 2017

(65) Prior Publication Data
US 2019/0242880 A1 Aug. 8, 2019

(30) Foreign Application Priority Data
Dec. 16, 2015 (FR) ................................ 1562528

(51) Int. Cl.
*G01N 33/50* (2006.01)
*G01N 33/68* (2006.01)
(Continued)

(52) U.S. Cl.
CPC ....... *G01N 33/5088* (2013.01); *C12N 5/0698* (2013.01); *C12Q 1/6883* (2013.01);
(Continued)

(58) Field of Classification Search
CPC ........... G01N 33/5088; G01N 33/6881; C12N 5/0698; C12Q 1/6883; C12Q 2600/148; C12Q 2600/158
See application file for complete search history.

(56) References Cited

U.S. PATENT DOCUMENTS

| 4,849,077 A | 7/1989 | Rosenthal et al. |
| 4,882,127 A | 11/1989 | Rosenthal et al. |

(Continued)

FOREIGN PATENT DOCUMENTS

| EP | 29678 B1 | 5/1983 |
| EP | 285471 B1 | 1/1991 |

(Continued)

OTHER PUBLICATIONS

Levi, Kamal, "Biomechanics of Human Stratum Corneum: Dry Skin Conditions, Tissue Damage and Alleviation", Philosophy, https://stacks.stanford.edu/file/druid:cb644mw1707/Levi%20Thesis%20Final%20Mod-augmented.pdf, 2009, p. i-xviii, pp. 1-154. (Year: 2009).*

(Continued)

*Primary Examiner* — Blaine Lankford
*Assistant Examiner* — Lauren K Van Buren
(74) *Attorney, Agent, or Firm* — Rouget F. Henschel; Potomac Law Group, PLLC

(57) ABSTRACT

The invention relates to biomarkers in children's skin, in particular in the skin of infants, the expression of which changes when the skin is dry. Such markers are particularly advantageous in that they allow the skin's response to dehydration to be monitored. The inventors have developed methods for evaluating the in vitro efficacy of formulations in preventing the effects of dehydration on children's skin, using a skin model specifically capable of reproducing the characteristics of children's skin.

5 Claims, 1 Drawing Sheet

(51) Int. Cl.
  *C12N 5/071* (2010.01)
  *C12Q 1/6883* (2018.01)
(52) U.S. Cl.
  CPC ... *G01N 33/6881* (2013.01); *C12Q 2600/148* (2013.01); *C12Q 2600/158* (2013.01)

(56) References Cited

U.S. PATENT DOCUMENTS

| | | | |
|---|---|---|---|
| 6,723,513 | B2 | 4/2004 | Lexow |
| 7,556,922 | B2 | 7/2009 | Block et al. |
| 2006/0275782 | A1 | 12/2006 | Gunderson et al. |
| 2007/0148771 | A1 | 6/2007 | Chopart et al. |
| 2008/0020392 | A1 | 1/2008 | Block et al. |
| 2009/0181385 | A1 | 7/2009 | McKernan et al. |
| 2009/0181860 | A1 | 7/2009 | McKernan et al. |
| 2009/0186249 | A1 | 7/2009 | Narendar |
| 2010/0099576 | A1 | 4/2010 | Comer et al. |
| 2015/0285787 | A1* | 10/2015 | Msika ............... G01N 33/5044 506/2 |
| 2015/0374605 | A1* | 12/2015 | Msika .................. A61K 31/22 424/59 |

FOREIGN PATENT DOCUMENTS

| | | |
|---|---|---|
| EP | 0296078 B1 | 5/1991 |
| EP | 1141399 A1 | 10/2001 |
| EP | 789074 B1 | 12/2003 |
| EP | 1878790 A1 | 1/2008 |
| EP | 1451302 B1 | 5/2008 |
| EP | 1974718 A1 | 10/2008 |
| FR | 2912916 B1 | 5/2009 |
| FR | 2945444 A1 | 11/2010 |
| FR | 2983868 A1 | 6/2013 |
| FR | 3019186 A1 | 10/2015 |
| FR | 3011008 B1 | 12/2017 |
| JP | J2010-172200 * | 8/2010 |
| WO | 0191821 A1 | 12/2001 |
| WO | 0192322 A1 | 12/2001 |
| WO | 02070729 A2 | 9/2002 |
| WO | 2003066896 A2 | 8/2003 |
| WO | 2004112742 A3 | 2/2005 |
| WO | 2005105123 A1 | 11/2005 |
| WO | 2005115421 A1 | 12/2005 |
| WO | 2006063864 A2 | 6/2006 |
| WO | 2006084132 A2 | 8/2006 |
| WO | 2006063865 A3 | 10/2006 |
| WO | 2007064305 A1 | 6/2007 |
| WO | 2007111924 A2 | 10/2007 |
| WO | 2008025847 A2 | 3/2008 |
| WO | 2011073281 A1 | 6/2011 |
| WO | 2014001749 A1 | 1/2014 |
| WO | 2014009566 A1 | 1/2014 |
| WO | 2014122326 A1 | 8/2014 |
| WO | 2014170495 A3 | 12/2014 |
| WO | 2015044230 | 6/2015 |
| WO | 2015104413 A1 | 7/2015 |

OTHER PUBLICATIONS

Boniface et al. "Oncostatin M Secreted by Skin Infiltrating T Lymphocytes Is a Potent Keratinocyte Activator Involved in Skin Inflammation" J. Immunol Apr. 1, 2007, 178(7) 4615-4622 (Year: 2007).*
Akiyama et al., "Spontaneous itch in the absence of hyperalgesia in a mouse hindpaw dry skin model," Neuroscience Letters, vol. 484, No. 1, pp. 62-65, Oct. 2010.
Auxenfans et al., "Adipose-derived stem cells (ASCs) as a source of endothelial cells in the reconstruction of endothelialized skin equivalents," Journal of Tissue Engineering and Regenerative Medicine, vol. 6, pp. 512-518, Jul. 2011.
Auxenfans et al., "Evolution of three dimensional skin equivalent models reconstructed in vitro by tissue engineering," Eur. J. Dermatol., vol. 19, No. 2, pp. 107-113, Mar./Apr. 2009.
Bechetoille et al., "Effects of Solar Ultraviolet Radiation on Engineered Human Skin Equivalent Containing Both Langerhans Cells and Dermal Dendritic Cells," Tissue Engineering, vol. 13, No. 11, pp. 2667-2679, 2007.
Black et al., "Optimization and Characterization of an Engineered Human Skin Equivalent," Tissue Engineering, vol. 11, No. 5/6, pp. 723-733, 2005.
Bouwstra et al., "Structural Investigations of Human Stratum Corneum by Small-Angle X-Ray Scattering," The Journal of Investigative Dermatology, vol. 97, No. 6, pp. 1005-1012, Dec. 1991.
Caspers et al., "In Vivo Confocal Raman Microspectroscopy of the Skin: Noninvasive Determination of Molecular Concentration Profiles," The Journal of Investigative Dermatology, vol. 116, No. 3, pp. 434-442, Mar. 2001.
Chiou et al., "Stratum Corneum Maturation: A Review of Neonatal Skin Function," Skin Pharmcol. Physiol., vol. 17, pp. 57-66, 2004.
Costin et al., "Vaginal Irritation Models: The Current Status of Available Alternative and In Vitro Tests," ATLA, vol. 39, pp. 317-337, 2011.
Dawhnhardt-Pfeiffer et al., "Noninvasive Stratum Corneum Sampling and Electron Microscopical Examination of Skin Barrier Integrity: Pilot Study with a Topical Glycerin Formulation for Atopic Dermatitis," Skin Pharmcol. Physiol., vol. 25, pp. 155-161, Mar. 2012.
Dayan et al., "Stratum Corneum: The Role of Lipids and Ceramides," Cosmetics & Toiletries, vol. 124, No. 2, pp. 37-44, 2006.
De Benedetto et al., "Tight junction defects in patients with atopic dermatitis," J. Allergy Clin. Immunol., vol. 127, No. 3, pp. 773-786, Mar. 2011.
Dongari-Bagtzoglou et al., "Development of a highly reproducible three-dimensional organotypic model of the oral mucosa," Nat. Protoc., vol. 1, No. 4, pp. 2012-2018, 2006.
Falcone et al., "Micropsectroscopic Confocal Raman and Macroscopic Biophysical Measurements in the in vivo Assessment of the Skin Barrier: Perspective for Dermatology and Cosmetic Sciences," Skin Pharmacol. Physiol., vol. 28, pp. 307-317, Sep. 2015.
Farwick et al., "Developments in Ceramide Identification, Synthesis, Function and Nomenclature," Cosmetics & Toiletries, vol. 124, vol. 2, pp. 63-72, Feb. 2009.
Fluhr et al., "Development and Organization of Human Stratum Corneum After Birth. Electron Microscopy Isotropy Score and Immunocytochemical Corneocyte Labelling as Epidermal Maturation's Markers in Infancy," British Journal of Dermatology, vol. 171, No. 5, pp. 978-986, Feb. 2014.
Fluhr et al., "Functional skin adaption in infacy—almost complete but not fully competent," Experimental Dermatology, vol. 19, No. 6, pp. 483-492, 2010.
Fluhr et al., "Infant epidermal skin physiology: adaptation after birth," British Journal of Dermatology, vol. 166, No. 3, pp. 483-490, 2012.
Fortunel et al., "Stem cells from human interfollicular epidermis: phenotypes and potentialities," J. Soc. Biol., vol. 202, No. 1, pp. 55-65, 2008.
Fuller et al., "The challenges of sequencing by synthesis," Nature Biotechnology, vol. 27, No. 11, pp. 1013-1023, 2009.
Gorcea et al., "Fourier transform infrared spectroscopy studies of lipid domain formation in normal and ceramide deficient stratum corneum lipid models," International Journal of Pharmaceutics, vol. 435, pp. 63-68, Nov. 2011.
Guenou et al., "Human embryonic stem cells derivative enable full reconstruction of the pluristratified epidermis," Lancet, vol. 374, No. 9703, pp. 1745-1753, 2009.
Henrikson et al., "The Relative Influences of Acidity and Polarity on Responsiveness of Small Organic Molecules to Analysis with Negative Ion Electrospray Ionization Mass Spectrometry (ESI-MS)," J. Am. Mass Spectrom., vol. 16, pp. 446-455, Feb. 2005.
Hogan et al., "Skin Barrier Function and Its Importance at the Start of Atopic March," Journal of Allergy, vol. 2012, Article ID 901940, 2012.
Hoste et al., "Caspase-14 is Required for Filaggrin Degradation to Natural Moisturizing Factors in the Skin," J. Invest. Dermatol., vol. 131, No. 11, pp. 2233-2241, 2011.

(56) References Cited

OTHER PUBLICATIONS

Iwai et al., "The Human Skin Barrier is Organized as Stacked Bilayers of Fully Extended Ceramides with Cholesterol Molecules Associated with the Ceramide Sphingoid Moiety," J. Invest. Dermatol., vol. 132, No. 9, pp. 2215-2225, Sep. 2012.
Jungersted et al., "Lipids and skin barrier fuction—a clinical perspective," Contact Dermatitis, vol. 58, pp. 255-262, 2008.
Kinikoglu et al., "Reconstruction of a full-thickness collagen-based human oral mucosal equivalent," Biomaterials, vol. 30, pp. 6418-6425, Aug. 2009.
Kinikoglu et al., "The influence of elasin-like recombinant polymer on the self-renewing potential of a 3D tissue equivalent derived from human lamina propria fibroblasts and oral epithelial cells," Biomaterials, vol. 32, pp. 5756-5764, May 2011.
Kraehenbuehl et al., "Three-dimensional biomaterials for the study of human pluripotent stem cells," Nature Methods, vol. 8, pp. 731-736, Aug. 2011.
Leclere-Bienfait et al., "Avocado perseose, a biomimetic active ingredient for the protection and accompaniment of infants' skin," Journal of Investigative Dermatology, vol. 133, p. S106, 2013.
Lequeux et al., "A Simple Way to Reconstruct a Human 3-D Hypodermis: A Useful Tool for Pharmacological Functionality," Skin Pharmocol. Physiol., vol. 25, pp. 47-55, Oct. 2011.
Mardis, "New strategies and emerging technologies for massively parallel sequencing: applications in medical research," Genome Medicine, vol. 1, No. 4, p. 40, 2009.
Masukawa et al., "Comprehensive quantification of ceramide species in human stratum corneum," Journal of Lipid Research, vol. 50, No. 8, pp. 1708-1719, 2009.
Metzker, "Sequencing technologies—the next generation," Nature Reviews Genetics, vol. 11, No. 1, pp. 31-46, Dec. 2009.
Michel et al., "Characterization of a New Tissue-Engineered Human Skin Equivalent With Hair," In Vitro Cell Dev. Biol.-Animal, vol. 35, pp. 318-326, Jun. 1999.
Miyamoto et al., "Itch-Associated Response Induced by Experimental Dry Skin in Mice," Jpn. J. Pharmacol., vol. 88, pp. 285-292, 2002.
Mosmann, "Rapid Colorimetric Assay for Cellular Growth and Survival: Application to Proliferation and Cytotoxicity Assays," Journal of Immunological Methods, vol. 65, pp. 55-63, 1983.
Nikolovski et al., "Barrier Function and Water-Holding and Transport Properties of Infant Stratum Corneum Are Different from Adult and Continue to Develop through the First Year of Life," Journal of Investigative Dermatology, vol. 128, pp. 1728-1736, 2008.
Nissan et al., "Functional melanocytes derived from human pluripotent stem cells engraft into pluristratified epidermis," PNAS, vol. 108, No. 36, pp. 14861-14866, Sep. 2011.
Petritis et al., "Ion-pair reversed-phase liquid chromatography for determination of polar underivatized amino acids using perfluroinated carboxylic acids as ion pairing agent," Journal of Chromotography A, vol. 833, pp. 147-155, 1999.
Pihlak et al., "Rapid genome sequencing with short universal tiling probes," Nature Biotechnology, vol. 26, No. 6, pp. 676-684, Jun. 2008.
Piraud et al., "Ion-pairing reversed-phase liquid chromatography/electrospray ionization mass spectrometric analysis of 76 underivatized amino acids of biological interest: a new tool for the diagnosis of inherited disorders of amino acid metabolism," Rapid Communications in Mass Spectrometry, vol. 19, pp. 1587-1602, 2005.
Ponec et al., "The Formation of Competent Barrier Lipids in Reconstructed Human Epidermis Requires the Presence of Vitamin C," The Journal of Investigative Dermatology, vol. 109, No. 3, p. 348-355, Sep. 1997.
Poumay et al., "A simple reconstructed human epidermis: preparation of the culture model and utilization in in vitro studies," Arch. Dermatol. Res., vol. 296, pp. 203-211, 2004.
Rosdy et al., "Retinoic Acid Inhibits Epidermal Differentiation When Applied Topically on the Stratum Corneum of Epidermis Formed In Vitro by Human Keratinocytes Grown on Defined Medium," In Vitro Toxicology, vol. 10, No. 1, pp. 39-47, Nov. 1997.
Schmalz et al., "Release of prostaglandin E2, IL-6 and IL-8 from human oral epithelial culture models after exposure to compounds of dental materials," Eur. J. Oral Sci., vol. 108, pp. 442-448, 2000.
Shendure et al., "Next-generation DNA sequencing," Nature Biotechnology, vol. 26, No. 10, pp. 1135-1145, Oct. 2008.
Shimizu, "Lipid Mediators in Health and Disease: Enzymes and Receptors as Therapeutic Targets for the Regulation of Immunity and Inflammation," Annu. Rev. Pharmacol. Toxicol., vol. 49, pp. 123-150, 2009.
Stamatas et al., "Infant skin physiology and development during the first years of life: a review of recent findings based on in vivo studies," International Journal of Cosmetic Science, vol. 33, pp. 17-24, 2011.
Sunwoo et al., "Physiological and Subjective Responses to Low Relative Humidity," Journal of Physiological Anthropology, vol. 25, pp. 7-14, 2006.
Telofski et al., "The Infant Skin Barrier: Can We Preserve, Protect, and Enhance the Barrier?," Dermatology Research and Practice, vol. 2012, Article ID 198789, 2012.
Vahlquist, "Markers of Skin Inflammation and Wound Healing," Acta Derm. Venereol., vol. 80, p. 161, 2000.
Valtcheva et al., "Enhanced non-peptidergic intraepidermal fiber density and an expanded subset of chloroquine-responsive trigeminal neurons in mouse model of a dry skin itch," J. Pain, vol. 16, No. 4, pp. 346-356, Apr. 2015.
Van Smeden et al., "LC/MS analysis of stratum corneum lipids: ceramide profiling and discovery," Journal of Lipid Research, vol. 52, pp. 1211-1221, 1991.
Vrana et al., "Development of a Reconstructed Cornea from Collagen-Chondroitin Sulfate Foams and Human Cell Cultures," Vis. Sci., vol. 49, No. 12, pp. 5325-5331, 2008.
Vyumvuhore et al., "Raman spectroscopy: in vivo quick response code of skin physiological status," Journal of Biomedical Optics, vol. 19, No. 11, p. 111603, Nov. 2014.
Yokota et al., "The possible involvement of skin dryness on alterations of the dermal matrix," Experimental Dermatology, vol. 23, Suppl. 1, pp. 27-31, 2014.
Honegger, "Overview of Cell and Tissue Culture Techniques," Current Protocols in Pharmacology, Supplement 4, pp. 12.1.1-12.1.12, 1999.
Frankart et al., "Epidermal morphogenesis during progressive in vitro 3D reconstruction at the air-liquid interface," Blackwell Publishing Experimental Dermatology, vol. 21,, pp. 871-875, 2012.
Rosdy et al., "Terminal Epidermal Differentiation of Human Keratinocytes Grown in Chemically Defined Medium on Inert Filter Substrates at the Air-Liquid Interface," Society for Investigative Dermatology, Inc., pp. 409-414, 1990.

\* cited by examiner

METHOD FOR EVALUATING THE EFFECTS OF DEHYDRATION ON CHILDREN'S SKIN

INTRODUCTION

The skin is a set of cells and macromolecules grouped together in the form of a resistant and flexible tissue, covering the entire body. It is formed of two joined layers, the epidermis and the dermis, with which subcutaneous tissues may be associated.

The epidermis, whose principal role is to protect the body, forms the uppermost layer of the skin and ensures the latter's impermeability and resistance. Four separate cellular layers can be identified in the skin: a basal layer (stratum basalis), a spinous layer (stratum spinosum), a granular layer (stratum granulosum) and a corneal layer (stratum corneum). While various cell types coexist in the epidermis, keratinocytes represent the large majority (90%). The characteristic activity of keratinocytes is synthesis of keratins, which are fibrous water-insoluble proteins making up 95% of all epidermal proteins.

The principal function of the skin is to establish a protective barrier against environmental attacks while allowing some exchanges between the internal environment and the external environment. The barrier function is provided first and foremost by the corneal layer (stratum corneum), which makes the skin impermeable and hydrophobic, thus protecting the dermis from a massive influx of water. The corneal layer also resists chemical attacks. This layer is composed of cells, called corneocytes, which are dead and anucleate but filled with keratins and other products such as lipids, fatty acids and ceramides. Corneocytes are joined together by specific tight junctions, corneodesmosomes, forming a compact layer whose cohesion is further strengthened by a lipid cement. Under the granular layer, the tight junctions of the granular layer also participate in the skin barrier function (see, for example, Hogan et al., *J Allergy*, 2012: 901940, 2012).

Each day the skin must deal with various attacks. It is exposed, for example, to chemical agents such as soap and to physical stresses such as friction against clothing and sun exposure. The epidermis and epidermal appendices must thus be constantly renewed to keep the skin in good condition. It is the stem cells which make these maintenance and repair processes possible. More particularly, the regenerative capacity of the epidermis is conferred by adult stem cells which enable the regular replacement of differentiated cells eliminated during keratinization. Epidermal stem cells thus give rise to keratinocytes, which ultimately differentiate into corneocytes, which themselves are exfoliated during the desquamation process. This process is particularly crucial for barrier function maturation and maintenance.

The barrier function is particularly important, especially for limiting epidermal water loss.

Indeed, regardless of skin type, it can undergo a temporary state of dehydration which may be linked to extrinsic factors (wind, cold, sun, detergents, etc.) and/or intrinsic factors (psoriasis, eczema, senescence, etc.). This lack of water leads to a decrease in the efficacy of the skin barrier. A cascade of events, called the "dry skin cycle", then occurs. First, the decrease in the barrier function leads to amplification of the decrease in water content and to barrier failure. In return, keratinocyte proliferation increases (hyperkeratosis) and moderate inflammatory changes are induced, the skin attempting to repair itself. This inflammatory hyperproliferative state is crucial in the dry skin cycle because it leads to aberrant differentiation and to production of materials and structures of poor quality. Lastly, the reduced activity of desquamation enzymes leads to a thickening and a loss of hygroscopy of the corneal layer.

Adaptation to extrauterine life is a process that begins at birth and continues throughout the first year of life. The first months of postnatal life constitute a period of structural and functional reorganization of the skin which allows physiological adaptation to the extrauterine environment. For example, the immaturity of the skin of newborns is underlined by the different structure and molecular composition of the stratum corneum compared with that of adults. These are incomplete and thus continue to develop during at least the first 12 months after birth (Chiou et al., *Skin Pharmacol Physiol*, 17:57-66, 2004; Nikolovski et al., *J Invest Dermatol*, 128:1728-1736, 2008; Stamatas et al., *Pediatr Dermatol*, 27:125-131, 2010; Telofski et al., *Dermatol Res Pract*, 2012:198789, 2012). Furthermore, the results of two recent clinical studies (Fluhr et al., *Br J Dermatol*, 166(3):483-90, 2012 and Fluhr et al., *Br J Dermatol*, 2014, doi:10.1111/bjd.12880) suggest that the skin of infants has a certain immaturity in its ability to capture water and to regulate the related mechanisms. Furthermore, this work showed that the epidermal barrier undergoes structural organization from birth to 2 years of age and is thus not completely competent during this period. This helps explain the fragility of infants' and young children's skin and its susceptibility to chemical, physical and microbial attacks.

Moreover, incomplete skin maturation can have significant clinical consequences. It is thus important to enable the skin to be built and to develop correctly and harmoniously, absent which its functional and structural organization may be compromised. In this respect, it is crucial to preserve the epidermis's barrier function and capacity of renewal.

Therefore, the immaturity of the barrier and of the mechanisms for regulating hydration in a baby's skin may make the baby even more vulnerable to the exogenous or endogenous factors involved in skin dryness.

There thus still remains a need, by integrating knowledge of children's skin and the role of dehydration, to identify and characterize active agents and improved formulations for providing the best care for children's dry skin.

DESCRIPTION

The present Inventors have shown that children's skin, and in particular infants' skin, is particularly sensitive to dehydration. In particular, they were able to identify biological markers whose expression is altered in dry skin. Such markers are particularly advantageous because they make it possible to follow the skin's response under drying conditions.

The Inventors have developed methods for evaluating the in vitro efficacy of active principles and formulations in preventing the effects of dehydration on children's skin, using a skin model specifically able to reproduce the features of children's skin, and in particular that of very young children such as infants. The studies of the prior art were based on the use of adult populations to analyse the skin's response to dehydration (De Benedetto et al., *J Allergy Clin Immunol.*, 127(3):773-786, 2011) or on models of adults' reconstructed skin (Yokota et al., *Exp Dermatol.*, 23 Suppl 1:27-31, 2014). However, the skin's properties evolve during the first years of life (see, for example, Fluhr et al., *Exp Dermatol.*, 19(6):483-492, 2010; Fluhr et al., *Br J Dermatol*, 166(3):483-90, 2012; and Fluhr et al., *Br J Dermatol.*, 2014, doi:10.1111/bjd.12880) and it is probably not possible to determine precisely the effects of dehydration on children's skin from samples of adults' skin.

On the other hand, the Inventors have developed reconstructed skin models derived from samples from children and were able to test the effect of dehydration on these models. They were thus able to observe that the expression of certain biological markers was altered when these children's reconstructed skin models were grown under drying conditions. Certain markers, such as inflammation markers, were thus more strongly expressed, whereas the expression of others, such as stem cell markers or those of the barrier function, was decreased. On the other hand, the variations of expression of these markers were reduced, or became less marked, when the models were treated with active agents or formulations known for treating or preventing dry skin. This result underlines the physiological relevance of these markers. The importance of the use of models of reconstructed skin from children and not from adults in order to isolate such markers therefrom is further reinforced.

The expression "dry skin", as used herein, refers to skin which has undergone water loss. Dry skin is rough, coarse, scaly and uncomfortable and is characterized by insufficient water in the corneal layer. Dry skin is also known to be xerotic skin.

Dry skin can be caused by prolonged exposure to low humidity so that dehydration stress increases to such an extent that the normal hydration gradient of the corneal layer is altered. In this respect, it has been shown that lower than 30% relative humidity in the atmosphere causes dry skin (Sunwoo et al., *J Physiol Anthropol,* 25:7-14, 2006). External conditions such as intense and dry cold, physical or chemical irritation, or sun exposure, for example, can trigger and/or maintain skin dehydration.

Dry skin can also develop following physical or chemical changes in the skin, such as ageing, leading to alteration of the normal hydration gradient. These changes can notably be caused by pathological situations, such as atopic dermatosis, for example.

The expression "drying condition", as used herein, refers to any condition which causes water to leave the skin. The drying conditions according to the invention are thus conditions which cause a normally hydrated children's skin model to become dry. Water can be caused to leave said model by external conditions in which the relative humidity in the atmosphere is lowered. It can also be caused by a direct alteration of the barrier function of the skin, for example by an alteration of natural moisturizing factors (NMFs) or of the lipid film of the corneal layer. The Inventors have shown that a children's skin model grown under conditions in which the relative humidity in the atmosphere is sharply lowered have physiological and histological features quite similar to those of children's dry skin. These dry skin models developed by the Inventors are particularly advantageous, since they make it possible to reproduce the children's dry skin phenotype as observed in vivo. These models are all the more advantageous in that other models causing water loss by alteration of the lipid layer do not make it possible to mimic the features of children's dry skin in vivo. Therefore, according to a preferred embodiment, the drying conditions according to the invention are conditions in which the relative humidity in the atmosphere is lowered relative to the usual skin cell culture conditions. More preferably, the relative humidity in the atmosphere is 50% or lower. Even more preferably, it is 45%, 40%, 35%, 30% or 25% or lower. According to a particularly preferred embodiment, it is 25% or lower.

The term "child", according to the invention, refers to an individual under 16 years of age. Therefore, the category of children according to the invention includes newborns aged 0 to 1 month, infants aged 1 month to 2 years, and children per se, aged at least 2 years. The term "newborn", as used herein, may equally well refer to a full-term or premature birth.

To remove any ambiguity, the term "child" used in the present application without any further clarification should be understood in the most general meaning thereof, i.e., as referring to a person under 16 years of age. An "adult" according to the present invention is a person who is not a child, in order words a person over 16 years of age.

Preferably, the method according to the invention may be used regardless of the ethnic or geographic origin of the skin, or the phototype thereof. It may thus be of Caucasian, African, Asian, South American, Melanesian or other origin; it may further have the phototype I, II, III, IV, V or VI, without affecting the invention. Indeed, the invention aims at identifying biological markers characterizing any skin type and depending only on the donor's age.

The methods of the invention are thus based on the use of a suitable skin model, reproducing children's skin, in particular children's dry skin, as well as the use of biological markers, the expression of which is affected by dehydration in a particular manner in children's skin. The invention thus makes it possible to determine precisely which active agents have an advantageous effect on the prevention or treatment of the effects of skin dehydration. The methods of the invention are also suitable for evaluating the activity of formulations. The Inventors were thus able to show that certain formulations were more effective than others in preventing and/or limiting the effects of dry skin, thus showing the utility of the approach undertaken.

According to a first aspect, the invention relates to a method for evaluating the in vitro efficacy of an active agent or of a formulation for preventing or treating the effects of dehydration of children's skin, said method comprising the determination of the level of expression and/or of activation of at least one biological marker.

More precisely, the method of the invention comprises preferentially the following steps:
  a) contacting said active agent or said formulation with a reconstructed skin model, said model being obtained from a skin sample from a child;
  b) growing the reconstructed skin model of step a) under drying conditions;
  c) measuring the expression level of at least one biological marker in the skin model of step b); and
  d) evaluating the efficacy of said active agent or of said formulation as a function of the level of step c).

In a first preferred embodiment, the reconstructed skin model is grown under drying conditions in step b) in the presence of the active agent or of the formulation. The Inventors have developed dry skin models grown in dry atmosphere which make it possible to reproduce the children's dry skin phenotype as observed in vivo. Therefore, according to another preferred embodiment, the drying conditions are cell culture conditions in which the relative humidity in the atmosphere is lowered relative to the usual skin cell culture conditions. More preferably, the relative humidity in the atmosphere is 50% or lower. Even more preferably, it is 45%, 40%, 35%, 30% or 25% or lower. According to a particularly preferred embodiment, it is 25% or lower. According to another preferred embodiment, the active agent or the formulation is removed prior to exposing said reconstructed skin model to drying during said step b).

Furthermore, the invention also relates to a method for evaluating the in vitro efficacy of an active agent or of a formulation in reducing the effects of dehydration on children's skin, characterized in that said method comprises the following steps:
- a) growing a reconstructed skin model under drying conditions, said model being obtained from a skin sample from a child;
- b) contacting said active agent or said formulation with the reconstructed skin model of step a);
- c) measuring the expression level of at least one biological marker in the skin model of step b); and
- d) evaluating the efficacy of said active agent or of said formulation as a function of the level of step c).

A person skilled in the art will easily understand that steps a) and b) can be performed simultaneously or successively, according to need. In other words, the reconstructed skin model can be grown under drying conditions in step b) in the presence of the active agent or of the formulation. Alternatively, the skin model can, first, be grown under drying conditions, then contacted with the active agent or the formulation.

The expression "the efficacy of a formulation or of an active agent in preventing or reducing the effects of dehydration of children's skin", within the meaning of the present application, refers to the ability of the formulation or of the active agent to cancel or decrease said effects of dehydration of children's skin. In this case, the term "prevention" refers to a treatment administered before the effects of dehydration develop, while "reduction" refers to a treatment administered once the effects of dehydration appear.

According to a preferred embodiment, the candidate formulation or the candidate active agent is effective for preventing, treating or reducing the effects of dehydration of children's skin if said candidate formulation or said candidate active agent makes it possible to increase or maintain the expression levels of at least one biological marker of the barrier function, and/or of at least one biological marker preferentially expressed in stem cells, and/or of at least one lipid, and/or at least one NMF. Alternatively or in combination, the candidate formulation or the candidate active agent is effective for preventing, treating or reducing the effects of dehydration of children's skin if said candidate formulation or said candidate active agent makes it possible to decrease or maintain the expression levels of at least one biological marker of inflammation.

According to a particularly preferred embodiment, the drying conditions are cell culture conditions in which the relative humidity in the atmosphere is lowered relative to the usual skin cell culture conditions. More preferably, the relative humidity in the atmosphere is 50% or lower. Even more preferably, it is 45%, 40%, 35%, 30% or 25% or lower. According to a particularly preferred embodiment, it is 25% or lower. According to a more preferred embodiment, the sample donor is more particularly a donor aged between 0 and 1 month, between 1 month and 2 years, or between 2 years and 16 years. In other words, according to this embodiment, the sample donor is selected from the group consisting of newborns aged between 0 and 1 month, of infants aged between 1 month and 2 years, and of children aged between 2 years and 16 years. More preferentially, the sample donor is a newborn or an infant.

In another embodiment, the expression level of said biological marker of step c) is compared with a reference expression level.

It is important to verify that the active agents and the formulations of the invention are well tolerated. For example, certain currently marketed products can cause irritation if used regularly. Such an effect can only worsen a developing or existing dry skin condition.

According to another aspect, the invention thus relates to a method for evaluating the tolerance of an active agent or of a formulation when children's skin becomes dry, said method comprising the following steps:
- a) contacting said active agent or said formulation with a reconstructed skin model, said model being obtained from a skin sample from a child;
- b) growing, under drying conditions, the reconstructed skin model of step a) in the presence of the active agent or of the formulation;
- c) measuring the expression level of at least one biological marker in the skin model of step b); and
- d) determining whether said active agent or of the formulation is well tolerated by children's skin as a function of the level of step c).

The method of the invention may further comprise a comparison of the cell viability in the reconstructed skin model treated with the active agent, the composition or the formulation and in the control reconstructed skin model, i.e., skin which is dehydrated but which has not been treated with the active agent or the formulation. In this case, the active agent or the cosmetic formulation is well tolerated by children's skin if the cell viability of the reconstructed skin model is not affected by the presence of the agent or the formulation.

According to another preferred embodiment, the method of the invention thus comprises an additional step of determining the cell viability in the reconstructed skin model which has been dehydrated and treated with the active agent or the cosmetic formulation, determining the cell viability of the control reconstructed skin model and comparing the two.

Many tests for determining cell viability are available to a person skilled in the art and are commonly used in cosmetics science. In particular, mention may be made of the MTT test, described for example in Mosman et al. (*J Immunol Methods*, 65(1-2):55-63, 1983).

According to a particularly preferred embodiment, the candidate formulation or the candidate active agent is well tolerated by children's skin if said candidate formulation or said candidate active agent makes it possible to increase or maintain the expression levels of at least one biological marker of the barrier function, and/or of at least one biological marker preferentially expressed in stem cells, and/or of at least one lipid, and/or at least one NMF. Alternatively or in combination, the candidate formulation or the candidate active agent is well tolerated by children's skin if said candidate formulation or said candidate active agent makes it possible to decrease or maintain the expression levels of at least one biological marker of inflammation.

According to another preferred embodiment, the drying conditions are cell culture conditions in which the relative humidity in the atmosphere is lowered relative to the usual skin cell culture conditions. More preferably, the relative humidity in the atmosphere is 50% or lower. Even more preferably, it is 45%, 40%, 35%, 30% or 25% or lower. According to a particularly preferred embodiment, it is 25% or lower.

In another embodiment, the expression level of said biological marker of step c) is compared with a reference expression level.

In another aspect, the invention makes it possible to isolate formulations or active agents having an effect in preventing the effects of dehydration of children's skin. As the experimental examples show, the invention makes it possible in particular to distinguish active agents or formulations according to their activity for preventing the effects of dehydration of children's skin. The invention thus is particularly suited to identifying appropriate formulations or active agents for this very specific skin type.

The invention thus also relates to a method for identifying an active agent or a formulation for preventing the effects of dehydration of children's skin, characterized in that said method comprises the following steps:
 a) contacting a candidate active agent or formulation with a reconstructed skin model, said model being obtained from a skin sample from a child;
 b) growing, under drying conditions, the skin model of step a);
 c) measuring the expression level of at least one biological marker in the skin model of step b); and
 d) determining whether said candidate active agent or formulation is a formulation or an active agent for preventing the effects of dehydration of children's skin as a function of the level of step c).

In a first preferred embodiment, the reconstructed skin model is grown under drying conditions in step b) in the presence of the active agent or of the formulation. According to another preferred embodiment, the active agent or the formulation is removed prior to exposing said reconstructed skin model to drying during said step b). According to another preferred embodiment, the drying conditions are cell culture conditions in which the relative humidity in the atmosphere is lowered relative to the usual skin cell culture conditions. More preferably, the relative humidity in the atmosphere is 50% or lower. Even more preferably, it is 45%, 40%, 35%, 30% or 25% or lower. According to a particularly preferred embodiment, it is 25% or lower.

Similarly, the method of the invention makes it possible to isolate active agents or formulations for reducing the effects of dehydration of children's skin. According to this embodiment, this method comprises the following steps:
 a) growing a reconstructed skin model under drying conditions, said model being obtained from a skin sample from a child;
 b) contacting a candidate active agent or formulation with the skin model of step a);
 c) measuring the expression level of at least one biological marker in the skin model of step b); and
 d) determining whether said candidate active agent or formulation is a formulation or an active agent for reducing the effects of dehydration of children's skin as a function of the level of step c).

A person skilled in the art will easily understand that steps a) and b) can be performed simultaneously or successively, according to need. In other words, the reconstructed skin model can be grown under drying conditions in step b) in the presence of the active agent or of the formulation. Alternatively, the skin model can, first, be grown under drying conditions, then contacted with the active agent or the formulation. According to a preferred embodiment, the drying conditions are cell culture conditions in which the relative humidity in the atmosphere is lowered relative to the usual skin cell culture conditions. More preferably, the relative humidity in the atmosphere is 50% or lower. Even more preferably, it is 45%, 40%, 35%, 30% or 25% or lower. According to a particularly preferred embodiment, it is 25% or lower.

In another embodiment, the expression level of said biological marker of step c) is compared with a reference expression level.

The candidate formulation is a formulation for preventing or reducing the effects of dehydration of children's skin if said candidate formulation makes it possible to modulate the expression of at least one biological marker of the invention. This modulation may correspond, as the case may be, and in particular according to the nature of the biological marker, to an increase or to a decrease in the expression of said marker. For example, it may be advantageous to isolate formulations minimizing the effects of dehydration on markers preferentially expressed in stem cells, said formulations making it possible to preserve the capacity of renewal of children's fragile skin. Similarly, it would be advantageous to identify formulations minimizing the effects of dehydration on barrier markers in children, in order to maintain the integrity of the skin barrier. Lastly, it may be desirable to isolate formulations that would not induce inflammation markers. Therefore, according to a preferred embodiment, the candidate formulation is a formulation for preventing or reducing the effects of dehydration of children's skin if said candidate formulation makes it possible to increase or maintain the expression levels of at least one biological marker of the barrier function, and/or of at least one biological marker preferentially expressed in stem cells, and/or of at least one lipid, and/or at least one NMF. Alternatively or in combination, the candidate formulation is a formulation for preventing or reducing the effects of dehydration of children's skin if said candidate formulation makes it possible to decrease or maintain the expression levels of at least one biological marker of inflammation.

Similarly, the candidate active agent is an active agent for preventing or reducing the effects of dehydration on children's skin if said candidate active agent makes it possible to modulate the expression of at least one biological marker of the invention. This modulation may correspond, as the case may be, and in particular according to the nature of the biological marker, to an increase or to a decrease in the expression of said marker. According to a preferred embodiment, the candidate active agent is an active agent for preventing or reducing the effects of dehydration of children's skin if said candidate active agent makes it possible to increase or maintain the expression levels of at least one biological marker of the barrier function, and/or of at least one biological marker preferentially expressed in stem cells, and/or of at least one lipid, and/or at least one NMF. Alternatively or in combination, the candidate active agent is an active agent for preventing or reducing the effects of dehydration of children's skin if said candidate active agent makes it possible to decrease or maintain the expression levels of at least one biological marker of inflammation.

First, the formulation or active agent of interest is contacted with a reconstructed skin culture obtained from a sample from a child. This contacting of the active agent of interest with the skin model may be made directly. Alternatively, it may be advantageous to formulate the active agent of interest, for example so as to obtain a liquid composition, in order to facilitate its contact with the skin model. Therefore, according to an embodiment of the invention, the method further comprises a step of formulating the active agent, in particular in the form of a liquid solution, in particular an aqueous solution, prior to the step of contacting said active agent with a skin model.

The Inventors previously showed that the expression profiles of specific categories of genes (for example, barrier, inflammation, defence and stem cell genes) evolve as a function of age (application WO 2014/009566). A person skilled in the art can thus easily characterize skin at the molecular level from birth to adulthood. More particularly, a person skilled in the art will note that children's skin cells have a specific expression profile of genes involved in specific physiological processes, in particular cell metabolism, the stress response, inflammation, immunity, apoptosis, growth/proliferation and the cell cycle, cell signalling, migration and differentiation, the epidermal barrier, adhesion and pluripotent stem cells of the skin.

In the meaning of the invention, the reconstructed skin model obtained from a skin sample from a child may be any tissue model comprising skin cells, in particular keratinocytes, and wherein said skin cells were obtained from a sample from a child.

The term "skin sample", in the meaning of the invention, refers to any sample containing skin cells. The skin samples according to the invention thus include fresh skin explants obtained directly from the patient, suspended skin cell cultures, monolayer skin cell cultures, bilayer skin cell cultures and tissue models, including reconstructed skin cultures and reconstructed mucosal cultures. As it is often difficult to work with fresh explants, it is particularly advantageous, within the scope of the present invention, to use skin cell cultures. Advantageously, the skin cells according to the invention comprise normal, healthy or diseased cells, or cells derived from lines. For example, the skin cells which are cultured may be cells obtained from a skin tissue explant. The term "explant" or "skin explant" as used herein refers to a sample of skin cells or tissue, which may be obtained for surgical purposes or for performing analyses.

In particular, an explant may be obtained during surgical excision. The term "excision" as used herein refers to a surgical procedure consisting of cutting (excising) a portion of skin of varying width and depth in order to treat a defect or excess growth thereof. Excision is performed either to remove a tumour known to be cancerous or suspected of being cancerous, or to treat an unwanted, benign skin defect for functional or cosmetic reasons. An excision according to the invention includes for example skin samples obtained after plastic surgery (mammoplasty, abdominoplasty, face-lift, foreskin removal, otoplasty, i.e., ear pinback, syndactyly or supernumerary fingers, etc.).

An explant may also be obtained by biopsy. The term "biopsy" as used herein refers to a sample of skin cells or tissue taken for analytical purposes. Several types of biopsy procedures are known and performed in the field. The most common types include (1) incisional biopsy, wherein only a tissue sample is taken; (2) excisional biopsy (or surgical biopsy) consisting of total ablation of a tumour growth, thus performing a therapeutic and diagnostic procedure, and (3) needle biopsy, wherein a tissue sample is taken with a needle, which may be wide or fine. Further types of biopsies exist, such as for example smears or curettage, and are also included in the present invention.

Alternatively, said skin cells may be obtained by stem cell differentiation (Guenou et al., *Lancet*, 374(9703):1745-1753, 2009; Nissan et al., *Proc. Natl. Acad. Sci.*, 108(36): 14861-14866, 2011; Kraehenbuehl et al., *Nature Methods*, 8:731-736, 2011).

The skin cells according to the invention, whether obtained from a biopsy or obtained by stem cell differentiation, include at least one type of cells habitually present in the hypodermis, dermis and/or epidermis. These cells thus include, among others, keratinocytes, melanocytes, fibroblasts, adipocytes, endothelial cells, mast cells, Langerhans cells and/or Merkel cells. Preferentially, the skin cells according to the invention include at least keratinocytes and/or fibroblasts. More preferentially, the skin cells according to the invention include keratinocytes and/or fibroblasts.

Numerous skin cell culture methods are known to a person skilled in the art. Any of these methods may be used to culture the skin cells according to the invention. Advantageously, the skin cells are cultured and/or stored under conditions which at least partially maintain cell metabolism and/or cell functions. The skin cell culture according to the invention thus equally includes suspended skin cell cultures, monolayer skin cell cultures, bilayer skin cell cultures and tissue models, including reconstructed skin cultures and reconstructed mucosal cultures.

For example, suspended skin cell cultures have been routinely employed in a great many laboratories, for several decades. Similarly, monolayer or bilayer skin cell cultures have been known and used for a very long time.

Furthermore, numerous tissue models, including in particular reconstructed skin models and reconstructed mucosal models (Rosdy et al., *In Vitro Toxicol.*, 10(1):39-47, 1997; Ponec et al., *J Invest Dermatol.*, 109(3):348-355, 1997; Ponec et al., *Int J Pharm.*, 203(1-2):211-225, 2000; Schmalz et al., *Eur J Oral Sci.*, 108(5):442-448, 2000; Black et al., *Tissue Eng*, 11(5-6):723-733, 2005; Dongari-Batgtzoglou and Kashleva, *Nat Protoc*, 1(4):2012-2018, 2006; Bechtoille et al., *Tissue Eng*, 13(11):2667-2679, 2007; Vrana et al., *Invest Ophthalmol Vis Sci*, 49(12):5325-5331, 2008; Kinicoglu et al., *Biomaterials*, 30(32):6418-6425, 2009; Auxenfans et al., *Eur J Dermatol*, 19(2):107-113, 2009; Kinicoglu et al., *Biomaterials*, 32(25):5756-5764, 2011; Costin et al., *Altern Lab Anim*, 39(4):317-337, 2011; Auxenfans et al., *J Tissue Eng Regen Med*, 6(7):512-518, 2012; Lequeux et al., *Skin Pharmacol Physiol*, 25(1):47-55, 2012; EP 29 678; EP 285 471; EP 789 074; EP 1 451 302 B1; EP 1 878 790 B1; EP 1 974 718; US 2007/0148,771; US 2010/0,099,576; WO 02/070729; WO 2006/063864; WO 2006/0,63865; WO 2007/064305) are available to a person skilled in the art and are included within the scope of the invention.

Advantageously, the tissue model comprises reconstructed skin models and reconstructed mucosal models. Preferably, the reconstructed skin model is selected from the group comprising dermis models, chiefly containing stromal cells, and more particularly fibroblasts, epidermis models essentially consisting of keratinocytes, hypodermis models, skin models including a dermis and an epidermis, and skin models comprising a dermis, an epidermis and a hypodermis. The models comprising at least a dermis form connective tissues, whereas the models comprising at least an epidermis form stratified epithelia composed of characteristic layers of the tissue in question. For example, in the epidermis models, it is possible to identify a basal layer (stratum basalis), a spinous layer (stratum spinosum), a granular layer (stratum granulosum) and a corneal layer (stratum corneum). Furthermore, preferably, the reconstructed mucosal model according to the invention is a mucosal model of the mouth, gum, vagina or cornea.

Advantageously, said model is a connective tissue model of dermal matrix comprising a matrix substrate preferably selected from:

an inert substrate selected from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane, a polyglycolic acid membrane or film.

This group includes for example the Skin²™ model ZK1100 and Dermagraft® and Transcyte® dermal models (Advanced Tissue Sciences);

- a cell culture-treated plastic (forming a dermal sheet: Michel et al., *In Vitro Cell. Dev Biol.-Animal,* 35:318-326, 1999);
- a gel or a membrane based on hyaluronic acid (Hyalograft® 3D-Fidia Advanced Biopolymers) and/or collagen (such as for example an equivalent dermis or collagen lattices) and/or fibronectin and/or fibrin; this group includes for example the Vitrix® dermal model (Organogenesis);
- an optionally surfaced porous matrix (for example an equivalent dermis), produced from collagen suitable for containing one or more glycosaminoglycans and/or optionally chitosan (EP0296078A1, WO 01/911821 and WO 01/92322).

This group also includes for example the Mimederm® dermal model (Coletica).

These matrix substrates comprise stromal cells, particularly fibroblasts.

Advantageously, said skin model is an epidermis model comprising a matrix substrate preferably selected from:

- an inert substrate selected from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane;

this group includes the Reconstructed Epidermis models (Skinethic®) and the EpiDerm® model (Mattek Corporation);

- a film or a membrane based on hyaluronic acid and/or collagen and/or fibronectin and/or fibrin.

In this group, particular mention may be made of the models: Laserskin® (Fidia Advanced Biopolymers), Episkin® (L'Oréal).

These models may be seeded with fibroblasts in the dermal portion.

These models, wherein fibroblasts may be optionally integrated, act as a substrate for keratinocyte inoculation and epidermis reconstruction. Advantageously, pigment cells, immunocompetent cells or nerve cells are introduced in addition to keratinocytes; preferably, the immunocompetent cells are Langerhans cells.

Advantageously, said tissue model is a reconstructed skin or mucosal tissue model comprising a dermal or chorion matrix substrate, preferably selected from:

- an inert substrate selected from the group consisting of a semi-permeable synthetic membrane, in particular a semi-permeable nitrocellulose membrane, a semi-permeable nylon membrane, a Teflon membrane or sponge, a polycarbonate or polyethylene, polypropylene, semi-permeable polyethylene terephthalate (PET) membrane, an inorganic semi-permeable Anopore, cellulose acetate or ester (HATF) membrane, a semi-permeable Biopore-CM membrane, a semi-permeable polyester membrane, said inert substrate optionally containing stromal cells, particularly fibroblasts,
- a gel based on collagen and/or hyaluronic acid and/or fibronectin, and/or fibrin comprising stromal cells, particularly fibroblasts,
- an optionally surfaced porous matrix, produced from collagen suitable for containing one or more glycosaminoglycans and/or optionally chitosan, these porous matrixes incorporating stromal cells, particularly fibroblasts,
- a de-epidermised dermis or dead dermis, of human or animal origin.

In this group, particular mention may be made of the following models: Mimeskin (Coletica), EpidermFT™, EpiAirway™, EpiOccular™ EpiOral™, EpiGingival™, EpiVaginal™ (MatTek corporation), Human Corneal Epithelium (HCE), Human Oral Epithelium (HOE), Human Gingival Epithelium (HGE), Human Vaginal Epithelium (HVE) (Skinethic®), Phenion® Full Thickness Skin Model (Phenion), Apligraf® (Organogenesis), ATS-2000 (CellSystems® Biotechnologie Vertrieb) and Skin²™ (ZK1200-1300-2000 Advanced Tissue Science).

Furthermore, models specifically intended for tissue therapy are available which may also be used within the scope of the present invention. Mention may be made of the Epidex (Modex Therapeutiques), Epibase® (Laboratoire Genevrier), Epicell™ (Genzyme), Autoderm™ and Transderm™ (Innogenetics) models.

The matrix substrate is then seeded with keratinocytes to reconstruct the epidermis and eventually obtain a reconstructed skin.

Advantageously, the skin model used comprises a model wherein at least one complementary cell type has been incorporated, such as endothelial cells (EC) and/or immune cells such as lymphocytes, macrophages, mast cells, dendritic cells and/or adipose cells and/or skin appendages, such as head and body hair, sebaceous glands.

After having exposed the reconstructed skin model of the invention to drying conditions, a person skilled in the art will be able to measure the expression level of the biological markers of the invention.

The term "biological marker", in the meaning of the present application, refers to a characteristic which is objectively measured and evaluated as an indicator of normal biological processes, of pathogenic processes, or of pharmacological responses to a therapeutic intervention. A biological marker thus refers to a whole range of various substances and parameters. For example, a biological marker may be a substance whose detection indicates a particular diseased state (for example the presence of activated protein C as a marker of infection), or conversely a substance whose detection indicates a specific physiological state. The biological marker according to the invention is preferentially a gene, gene products such as gene transcripts and peptides derived from gene transcripts, a lipid, a sugar or a metabolite.

According to an embodiment of the present invention, the biological marker is a gene, gene products such as transcripts or peptides, a lipid, a sugar or a metabolite whose changes in expression, in particular the expression level, correlate with a physiological state of children's skin.

A person skilled in the art seeking to determine the class to which a genetic or protein marker belongs can easily consult the relevant scientific literature or refer to public databases such as, for example, those contained in the National Center for Biotechnology Information website (http://www.ncbi.nlm.nih.gov/guide/).

The Inventors particularly selected markers whose expression level varies after dehydration in a surprising and unexpected manner in children. The selected markers thus have a particular advantage within the scope of the method of the invention, insofar as their expression level is measured on a skin model reproducing the features of children's skin.

The Inventors have shown in particular that the drying conditions affected the amount of lipids and of NMFs produced by a children's skin model. Moreover, the Inventors have shown that, at the same time, expression of barrier markers, as well as markers of NMF synthesis, decreases. Lastly, stem cell markers, and consequently the skin's capacity of renewal, are also affected. On the other hand, contacting the skin with a formulation active against the effects of skin dehydration makes it possible to prevent and correct the variations of expression of said markers, which underlines their relevance.

The biological marker of the invention is thus advantageously a marker selected from the group of stratum corneum lipids, notably ceramides, NMFs, inflammation markers, barrier function markers and markers preferentially expressed in stem cells.

The Inventors have shown in particular that the amount of skin lipids decreased when the children's skin model was grown under drying conditions. In the corneal layer, lipids are arranged in lamellar planes in the spaces between the corneocytes, thus forming a cement that helps to protect the skin against external aggressions and to maintain a satisfactory intraepidermal water level. These lipids are phospholipids, cholesterol and glucosylceramides, which are modified, in the intercorneocyte spaces, by specialized enzymes, into ceramides, cholesterol, cholesterol sulphate and free fatty acids. (Jungersted et al., *Contact Dermatitis*, 58(5): 255-262, 2008). Ceramides, sterols and free fatty acids are also found in the sebum, among other components. Lastly, the skin surface is covered with a protective film which allows the skin to maintain its hydration and to protect itself from external aggressions. This superficial skin film includes, among other things, a hydrolipidic film essentially comprised of sweat, water, sebum and other lipids. These include ceramides, triglycerides and fatty acids, in roughly equal proportions.

According to a particular embodiment, the biological marker according to the invention is thus a lipid marker. The term "lipids", as used herein, refers to any liposoluble (i.e., lipophilic) natural molecule. Lipids are a heterogeneous group of compounds having many essential biological functions. Lipids can be defined more particularly as small hydrophobic or amphiphilic molecules, which come wholly or partly from ketoacyl or isoprene groups. For an overview of all lipid classes, refer to "Lipid Metabolites and Pathways Strategy (LIPID MAPS) classification system" (National Institute of General Medical Sciences, Bethesda, MD). In particular, the lipid marker according to the invention is selected from ceramides, phospholipids, glucosylceramides, sterols, triglycerides and free fatty acids. More preferably, the lipid marker according to the invention is selected from ceramides.

A "ceramide" according to the invention is a lipid derived from the amidification reaction of sphingosine and a fatty acid. A ceramide thus consists of a sphingosine or phytosphingosine base linked by an amide bond to $\alpha$-hydroxy, $\omega$-hydroxy or non-hydroxy acids having variable hydrophobic chain lengths. In the human stratum corneum, 9 ceramide classes, denoted CER1 to CER9, have been identified (see, for example, Dayan, *Cosm & Toil*, 121(1):37-44, 2006; Jungersted et al., *Contact Dermatitis*, 58(5):255-262, 2008; Farwick et al., *Cosm & Toil*, 124(2):63-72; Masukawa et al., *J Lipid Res.*, 50(8):1708-1719, 2009). The ceramide according to the invention is selected more preferentially from the group consisting of said ceramides CER1 to CER9.

Furthermore, the present Inventors have shown that NMFs were affected by the drying conditions. Natural moisturizing factor (NMF) derives from the proteolysis of filaggrin by a cascade of reactions involving enzymes which include, notably, caspase 14 and peptidylarginine deiminase (PAD1). NMF is a mixture of hygroscopic substances having the property of retaining water (Fluhr et al., *Exp Dermatol.*, 19(6):483-492, 2010). Among these, the sodium salt of pyrrolidone carboxylic acid (NaPCA; from cyclization of glutamic acid released by decomposition of profilaggrin) and the lactates are the most hygroscopic substances. NMF further comprises free amino acids (serine, citrulline, etc.), citrates and formates, urea, ions, nitrogen, uric acid, glycosamine, creatinine, phosphates, and yet unidentified compounds. The amount of NMF can be measured by all methods known to a person skilled in the art, notably by Raman microspectroscopy. According to another preferred embodiment, the biological marker according to the invention is therefore NMF.

The Inventors have thus shown that inflammation markers are particularly expressed after children's skin has been incubated in dry atmosphere. Inflammation is a normal defence reaction of the organism, but it can contribute to decreased skin integrity. Moreover, the Inventors have shown that, at the same time, dehydration induces in a children's skin model decreased expression of barrier function markers and of markers preferentially expressed in stem cells.

The expression "skin inflammation markers", in the meaning of the invention, refers to markers whose variation of expression correlates with skin inflammation.

The term "inflammation" according to the invention refers to the set of defence reaction mechanisms by which the body recognizes, destroys and eliminates all foreign substances. "Skin inflammation" corresponds more particularly to an immune system reaction to an attack on the skin, such as an environmental attack, optionally causing a wound, even vascular damage as the case may be. Skin inflammation may appear as an erythema, characterized by redness associated with local vasodilatation, an oedema, characterized by swelling, and a sensation of heat. Moreover, skin inflammation is accompanied by a variation of expression level or concentration of genetic or protein markers well-known to a person skilled in the art, who can refer, for example, to Vahlquist (*Acta Derm Venereol;* 80:161; 2000).

The triggering and the progression of the inflammation, and its diffusion from the initial source, require factors which are synthesized locally or which are in the inactive precursor state in the bloodstream. Specific processes in the inflammation reaction can be differentiated according to the mediator type synthesized. Thus, the skin inflammation according to the invention includes at least three distinct processes: protein inflammation, lipid inflammation and neurogenic inflammation.

The term "protein inflammation" or "aspecific inflammation" as used herein refers to the production, in response to an external attack, of protein inflammatory mediators, such as cytokines IL-1, IL-2, IL-6, IL8 and TNFα, the complement system, or proteins involved in coagulation, as the case may be. The term "lipid inflammation" as used herein refers to the production to said external attack of lipid mediators, in particular prostaglandins and leukotrienes, both synthesized from arachidonic acid, as well as activation of the enzymes responsible for this production (Shimizu, *Annu Rev Pharmacol Toxicol.*, 49:123-150, 2009). The protein and lipid mediators thus produced will induce a reaction cascade within the skin involving other inflammatory cells, in particular immune and vascular cells. The clinical result is expressed particularly by redness or oedema.

In response to an external attack, the neurosensory system may be stimulated and associated with the inflammatory reaction then implementing other cellular actors such as nerves (or nerve endings) and cells such as mast cells. The term "neurogenic inflammation" as used herein refers to the release by nerve endings, in response to an external attack, of specific mediators, in particular neuropeptides (in particular tachykinins including substance P, and calcitonin gene-related peptide (CGRP)); also participating in the neurogenic inflammation according to the invention is the activity of particular receptors such as the substance P receptor or the receptor TRPV1. Neurogenic inflammation most often results in a sensation of pain and/or discomfort and/or of itching (pruritus).

The skin inflammation marker according to the invention is preferably selected from protein inflammation markers, lipid inflammation markers and neurogenic inflammation markers.

Preferentially, the protein inflammation marker is selected from the group consisting of interleukins, preferably IL1α and IL8. Human interleukin IL1α has a protein sequence represented by the sequence having NCBI reference: NP_000566. This protein is encoded by the human IL1A gene (NCBI reference: Gene ID: 3552), the sequence of which corresponds to NCBI reference: NM_000575. The protein sequence of human interleukin IL-8 corresponds to the sequence having NCBI reference: NP_000575. This protein is encoded by the human IL8 gene (NCBI reference: Gene ID: 3576). The sequence thereof is accessible under NCBI reference: NM_000584.

Nerve growth factor receptor (NGFR) has a protein sequence represented by reference sequence NP_002498. This protein is encoded by the NGFR gene (NCBI reference: Gene ID: 4804). Its sequence is accessible under NCBI reference: NM_002507.

OSMR (oncostatin-M-specific receptor subunit beta, or oncostatin M receptor) is a type I cytokine receptor, the ligand of which is oncostatin. The OSMR protein corresponds to the sequence represented by the GenBank accession number NP_001161827, and is encoded by the OSMR gene (NCBI reference: Gene ID: 9180), having sequence NM_001168355.

The protein F2RL1 (coagulation Factor II (thrombin) receptor-like 1), which is also called PAR2 (protease-activated receptor 2) or GPR11 (G-protein-coupled receptor 11) is a receptor encoded by the F2RL1 gene (NCBI reference: Gene ID: 2150) in human.

This receptor, a member of the family of seven-transmembrane-domain receptors or GPCR, plays a role in modulation of inflammatory responses. The sequence of this protein is accessible under NCBI reference: NP_005233, whereas the F2RL1 gene sequence can be obtained with the GenBank accession number NM_005242.

The lipid inflammation marker is advantageously selected from prostaglandins, including in particular prostaglandin E2, and enzymes of the synthesis thereof from arachidonic acid, in particular PTGS2.

Prostaglandin E2 (PGE2) is a well-known arachidonic acid derivative obtained by the action of cyclooxygenase. Two isoforms of cyclooxygenase (COX) exist: cyclooxygenase 1, which is constitutive in tissues, and cyclooxygenase 2, which is induced by inflammatory phenomena. Proinflammatory stimulation (trauma, cytokines, etc.) thus lead to the synthesis of PGE 2, which is responsible for vasodilatation (generating redness and oedema), sensitization of nociceptors to bradykinin and histamine (responsible for pain) and fever (with cytokines IL1 and IL6).

The enzyme cyclooxygenase 2, also called prostaglandin-endoperoxide synthase (PTGS), is encoded by the human PTGS2 gene (NCBI reference: Gene ID: 5743). The sequence of this gene is available under NCBI reference: NM_000963 and the protein sequence under NCBI reference: NP_000954.

Preferably, the marker of neurogenic inflammation is selected from neuropeptides and neuropeptide receptors, in particular the receptors TRPV1 and SPR. The receptor TRPV1 (transient receptor potential vanilloid-1) is a cation-channel type membrane protein of the TRP family having the sequence with NCBI reference: NP_061197. In the skin, TRPV1 is expressed by keratinocytes, mast cells and nerve fibres. In response to an aggressor, TRPV1 activation leads to the production of cytokines and neuropeptides and is an actor in neurogenic inflammation. The gene encoding TRPV1 is the TRPV1 gene (NCBI reference: Gene ID: 7442), the sequence of which has the NCBI reference: NM_018727. The TRPV3 gene, (NCBI reference: Gene ID: 162514), the sequence of which has the NCBI reference: NM_001258205, encodes a receptor of the same family as TRPV1. The sequence of this TRPV3 corresponds to reference sequence NP_001245134.

Protachykinin-1 is a protein encoded in human by the TAC1 gene (NCBI reference: Gene ID: 6863), the sequence of which has the NCBI reference: NM_003182. The sequence of this protein is accessible under NCBI reference: NP_003173. SPR (substance P receptor; also known as neurokinin 1 receptor, NK1R, or tachykinin receptor 1, TACR1) is a G protein-coupled receptor (GPCR) which transmits the signal of substance P (SP) and other tachykinins. It is encoded by the human TACR1 gene, the sequence of which has the NCBI reference: NM_001058. Its peptide sequence is the sequence having NCBI reference: NP_001049.

MRGPRD is a receptor of the family of seven-transmembrane-domain receptors, so called GPCR. MRGD (MAS-related G-protein-coupled receptor member D) is more particularly expressed in a subpopulation of sensory neurons which participate in pain detection. This receptor is encoded by the gene is encoded by the human MRGPRD gene (NCBI reference: Gene ID: 116512). The sequence of this gene is available under NCBI reference: NM_198923 and the protein sequence under NCBI reference: NP_944605.

Phospholipases A2 are a family of enzymes which release pro-inflammatory mediators (lysophospholipids, oxidized fatty acids) by hydrolysis of short-chain oxidized phospholipids present on oxidized low-density lipoproteins (LDL). Among these, phospholipase A2 group IIF is encoded by the human PLA2G2F gene (NCBI reference: Gene ID: 64600). The sequence of this gene is available under NCBI reference: NM_022819 and the protein sequence under NCBI reference: NP_073730.3.

According to the invention, the skin inflammation marker is thus preferably selected from the group consisting of IL1A, IL8, PTGS2, NGFR, TAC1, TAC1R, TRPV1, TRPV3, MRGPRD, OSMR, PLA2G2F and F2RL1.

The present Inventors have further shown that dehydration induces a decrease in the expression of barrier function markers and markers preferentially expressed in stem cells.

The "barrier markers" according to the invention comprise markers which are expressed specifically in the outermost layers of the epidermis and which participate in the barrier function.

As a person skilled in the art well knows, the main function of the skin is to establish a protective barrier against environmental attacks while allowing certain exchanges between the internal environment and the external environment. This barrier function is chiefly provided by the stratum corneum of the epidermis. Intercellular lipids and corneodesmosomes, and the cornified envelope of corneocytes, are the key components.

However, beneath the stratum corneum, tight junctions constitute a second line of the barrier function. These junctions constitute in the stratum granulosum a selective paracellular diffusion barrier preventing penetration of harmful molecules. Tight junctions are made up of various transmembrane proteins such as, in particular, claudins, occludin and ZO1.

The barrier functions provided by the stratum corneum and the tight junctions are closely linked. Indeed, the alteration of one can influence the formation of the other.

Preferentially, the barrier function markers according to the invention are markers expressed in the stratum corneum or markers expressed in the tight junctions of the stratum granulosum. In a more preferential embodiment, said epidermal barrier marker is selected from the group consisting of desmoglein 1 (DSG), sciellin (SCEL), peptidyl arginine deiminase 1 (*PADI*1), caspase 14 (CASP14), loricrin (LOR), transglutaminase 1 (TGM1) and claudin 1 (CLDN1).

The corneodesmosome is the only junction structure of the corneal layer, which underlines the importance of this structure for maintaining corneal layer integrity. Desmoglein 1 is a constitutive protein of corneodesmosomes the sequence of which is available under reference NP_001933. The DSG1 gene (NCBI reference: Gene ID: 1828) encodes desmoglein-1 and has reference sequence NM_001942. Sciellin, having sequence NP_001154178, and encoded by the SC gene (NCBI reference: Gene ID: 8796), itself having sequence NM_001160706, is a precursor of the cornified envelope. Loricrin is a major protein component of the cornified envelope, of which it makes up roughly 70% by mass. This protein has sequence NP_000418 and is encoded by the LOR gene (NCBI reference: Gene ID: 4014) having sequence NM_000427. The formation of bonds between the protein components of the envelope of the cornified envelope is provided by the enzyme transglutaminase 1. The sequence of this enzyme corresponds to that which can be found under reference NP_000350. The TGM1 gene (NCBI reference: Gene ID: 7051) encodes desmoglein-1 and has reference sequence NM_000359.

Tight junctions represent one mode of cell adhesion, in epithelial tissues. They block the circulation of fluids between cells and thus ensure impermeability between two tissue compartments. They are located at the apex of epithelial cells where they form a continuous band around which impermeability is provided. The CLDN 1 gene (NCBI reference: Gene ID: 9076) encodes the claudin 1 protein, which is one of the most important components of tight junctions. This protein has a sequence corresponding to that of NCBI reference NP_066924. The CLDN1 gene sequence is accessible under reference NM_021101.

Barrier markers also include markers of NMF metabolism and of intercorneocyte lipids. These compounds allow water to be retained in the epidermis as it rises towards the corneal layer. Peptidylarginine deiminase 1 (PADI1) and caspase 14 (CASP14) are two enzymes involved in the maturation of filaggrin allowing production of NMF. Peptidylarginine deiminase 1, having sequence NP_037490, is an enzyme which removes an imine function on filaggrin and keratin K1, which maintains hydration of the stratum corneum, and consequently the skin barrier function. This enzyme is encoded by the PADI1 gene, the sequence of which (NCBI reference: Gene ID: 29943) can be found under reference NM_013358. Caspase-14, a member of the caspase family, is necessary for degradation of filaggrin to NMF (Hoste et al., *J Invest Dermatol.* 131(11):2233-2241, 2011). This protein, having sequence NP_036246, is encoded by the CASP14 gene (NCBI reference: Gene ID: 23581), the sequence of which is under reference NM_012114.

The expression "markers preferentially expressed in stem cells" according to the invention refers to the markers, and more specifically to the genes and proteins, which are specifically present in epidermal stem cells.

The expression "stem cell of the epidermis" or "epidermal stem cell", in the meaning of the present invention, refers to an epidermal cell capable of long-term renewal. The epidermal stem cells of the invention comprise, among others, follicular stem cells, sebaceous stem cells and basal stem cells, the latter also being called interfollicular epidermal stem cells. The terms "follicular stem cells", "sebaceous stem cells" and "basal stem cells", in the meaning of the invention, refer to stem cells located in the region of the hair follicle bulge, in sebaceous glands and in the basal layer of the epidermis, respectively. In a preferential embodiment of the invention, the epidermal stem cells of the invention are basal stem cells.

More precisely, the term "epidermal stem cell", in the meaning of the present invention, refers to a cell endowed with a high potential for long-term renewal. The term "potential for renewal" as used herein refers to the capacity to undergo at least one cell division cycle. A "high potential for long-term renewal" thus represents a cell's capacity to enter several successive cell division cycles. It is well-known that cells differentiated from the skin are not capable of carrying out several successive divisions (Fortunel and Martin, *J Soc Biol,* 202(1):55-65, 2008). It is understood herein that "successive" does not mean "consecutive" and that there may be periods during which a stem cell according to the invention remains quiescent without however losing its high potential for long-term renewal.

Conservation of a high potential for long-term renewal is expressed by asymmetrical division producing two different cells. The first daughter cell is a stem cell identical to the parent stem cell, while the second is a transit amplifying cell that divides in a limited manner over a short period of time and then enters the differentiation process. Advantageously, the epidermal stem cells of the invention are thus further capable of generating at least one type of epidermal cell by differentiation. In other words, the transit amplifying cell is capable of giving rise to at least one type of epidermal type by differentiation. Preferentially, said epidermal cell is a keratinocyte. More preferentially, the transit amplifying cell is capable of giving rise to all the types of epidermal cells by differentiation.

Preferentially, the markers expressed in stem cells are markers that participate in stem cell functions and protection. Mention may be made, for example, of the markers ΔNp63, BIRC5 (survivin), FN1 (fibronectin 1), MCSP (melanoma-associated chondroitin sulphate proteoglycan), LRIG1 (leucine-rich repeats and immunoglobulin-like domains protein 1), GJA1 (connexin 43), NID1 (nidogen 1), KRT15 (keratin 15), KRT19 (keratin 19), EGFR (epidermal growth factor receptor), CD71 (transferrin receptor), DSG3

(desmoglein 3), ITGB1BP1 (integrin beta1 binding protein), ITGA6 (integrin alpha 6), ITGB1 (integrin beta1) and ITGB4 (integrin beta 4) or markers involved in the signalling and regulation of stem cell activity such as Wnt/beta catenin, sonic hedgehog (SHH), NOTCH1 (notch homolog 1, translocation-associated). ΔNp63 and survivin are markers of resistance to apoptosis, thus having a role in stem cell survival. Cytokeratins 15 and 19 are positive stem cell markers, cytokeratin 15 being a marker of their survival. MCSP colocalizes with integrins in non-dividing cells, whereas integrin beta1 (marker of basal membrane adhesion to the extracellular matrix) and integrin alpha 6 (constituting hemidesmosomes, marker of keratinocytes binding together) are surface proteins that take part in intercellular communication, regulating the differentiation/proliferation processes as well as interaction with the niche. Transferrin receptor (CD71) is a known surface marker for stem cells which is used to isolate, in a population of integrin alpha6-positive cells, cells with high clonogenic capacity. Finally, Lrig1 is an epidermal growth factor receptor (EGFR) antagonist, thus maintaining quiescent stem cells, whereas, in contrast, EGFR, which is a marker whose absence characterizes stem cells, leads the cells down the proliferation pathway.

Preferentially, the marker preferentially expressed in stem cells is selected from the group consisting of markers ΔNp63, KRT15 (keratin 15), KRT19 (keratin 19), BIRC5 (survivin), and NOTCH1 (Notch homolog 1). These markers are well-known to a person skilled in the art. The KRT15 (NCBI reference: Gene ID: 3866), KRT19 (NCBI reference: Gene ID: 3880), BIRC5 (NCBI reference: Gene ID: 332) and NOTCH1 (NCBI reference: Gene ID: 4851) genes thus correspond to the sequences represented by the following GenBank accession numbers, respectively: NM_002275, NM_002276, NM_001012270, and NM_017617. The keratin 15, keratin 19, survivin and Notch homolog 1 proteins, for their part, correspond to the sequences represented by the following GenBank accession numbers, respectively: NP_002266, NP_002267, NP_001012270 and NP_060087. ΔNp63 protein is an isoform of TP63 (tumour protein 63) obtained by transcription from an internal promoter located in an intron. This protein corresponds to the sequence represented by the GenBank accession number: NP_001108452, and is encoded by the TP63 gene (NCBI reference: Gene ID: 8626), the sequence of which is available under the following GenBank accession number: NM_001114980.

It will be further evident to a person skilled in the art that the method of the invention will allow an evaluation of the efficacy of the formulation or of the active agent which will be all the more complete when a large number of markers of different types are used.

According to a preferred embodiment, the method of the invention comprises a step c) of measuring the expression level of a combination of biological markers. Said combination according to the invention comprises at least two markers, said markers being selected from at least two different marker categories described above: NMF, lipids, notably including ceramides, inflammation markers, barrier markers and stem cell markers. According to a preferred embodiment, said combination includes more than two markers. According to a more preferred embodiment, each marker belongs to a distinct marker category described above. It is also possible to use combinations of markers as defined above, wherein certain marker classes are represented by more than one marker.

The use of combinations of markers comprising at least one marker of each of the various types indicated above is particularly advantageous.

For each of these markers, the term "expression level" refers to the cellular concentration of said marker. Therefore, the expression level of ceramides corresponds to the concentration of said lipids in the cell. If the marker is a gene, the "expression level" in the meaning of the invention corresponds to the cellular concentration of at least one product of the gene of said marker. More precisely, the expression level of said biological marker corresponds to the amount or to the cellular concentration of the transcript of said gene or of the protein derived from said transcript. According to a preferred embodiment, the expression level of said biological marker corresponds to the amount or to the cellular concentration of the transcript of said gene. According to another embodiment, the expression level of said biological marker corresponds to the amount or to the cellular concentration of the protein derived from said transcript.

The expression "measuring the expression level of a combination of biological markers", in the meaning of the present application, refers to measuring the expression level of each marker of the combination. The expression of a gene may be measured for example at the nucleotide level, by measuring the amount of transcripts of said gene, and may also be measured for example at the peptide level, by measuring for example the amount of proteins derived from said transcript. Thus, the expression "measuring the expression level of said gene", in the meaning of the invention, refers to measuring the amount of the gene product in its peptide form or its nucleotide form.

Generally, the expression of the biological marker according to the invention will be detected in vitro from the reconstructed skin model.

In a particular embodiment, the method of the invention may comprise one or more intermediate steps between obtaining the reconstructed skin model and measuring the expression of the biological marker, said steps corresponding to extracting from said reconstructed skin model a lipid sample, an NMF sample, an mRNA (or corresponding cDNA) sample or a protein sample. Said sample may then be used directly to measure the expression of the marker. The preparation or extraction of mRNA (and the reverse transcription thereof into cDNA), of proteins, of lipids or of NMF from a skin cell sample is a routine procedure well-known to a person skilled in the art.

Once an mRNA (or corresponding cDNA) or protein sample is obtained, expression of the marker, in terms either of mRNA (i.e., in all the mRNA or cDNA present in the sample) or of proteins (i.e., in all the proteins present in the sample), can be measured. To that end, the method used thus depends on the type of transformation (mRNA, cDNA or protein) and on the type of sample available.

When expression of the marker is measured at the mRNA (or the corresponding cDNA) level, any technology commonly used by a person skilled in the art may be used. These technologies for analysing levels of gene expression, such as transcriptome analysis, for example, include well-known methods such as PCR (polymerase chain reaction, if starting with DNA), RT-PCR (reverse transcription-PCR, if starting with RNA) and quantitative RT-PCR, or nucleic acid chips (including DNA chips and oligonucleotide chips) for higher throughput.

The term "nucleic acid chips" as used herein refers to several different nucleic acid probes attached to a substrate, which may be a microchip, a glass slide or a microspheresize bead. The microchip may be composed of polymers, plastics, resins, polysaccharides, silica or a material containing silica, carbon, metals, inorganic glass or nitrocellulose.

The probes may be nucleic acids such as cDNA (cDNA chips), mRNA (mRNA chips) or oligonucleotides (oligonucleotide chips), said oligonucleotides typically having a length of between roughly 25 and 60 nucleotides.

To determine the expression profile of a particular gene, a nucleic acid corresponding to all or part of said gene is labelled and then contacted with the chip under hybridization conditions, leading to the formation of complexes between said labelled target nucleic acids and probes complementary to this nucleic acid attached to the surface of the chip. The presence of the labelled hybrid complexes is then detected.

These technologies make it possible to follow the expression level of one gene in particular or of several genes, and even of all the genes of the genome (full genome or full transcriptome) in a biological sample (cells, tissues, etc.). These technologies are used routinely by a person skilled in the art and therefore it is not necessary to detail them herein. Exemplary implementations of the invention based on analysis of gene expression (cDNA chips) and on quantitative PCR are described in the experimental section.

Alternatively, it is possible to use any current or future technology making it possible to determine the expression of genes on the basis of the amount of mRNA in the sample. For example, a person skilled in the art can measure the expression of a gene by hybridization with a labelled nucleic acid probe, such as, for example, with a Northern blot (for mRNA) or a Southern blot (for cDNA), but also by techniques such as the serial analysis of gene expression (SAGE) method and derivatives thereof, such as LongSAGE, SuperSAGE, DeepSAGE, etc. It is also possible to use tissue chips (also known as tissue microarrays, or TMAs). The tests commonly employed with tissue chips include immunohistochemistry and fluorescent in situ hybridization. For the analysis of mRNA levels, tissue chips may be coupled with fluorescent in situ hybridization. Finally, it is possible to use massively parallel sequencing to determine the amount of mRNA in the sample (RNA-Seq, or whole transcriptome shotgun sequencing). For that purpose, several methods of massively parallel sequencing are available. Such methods are described in, for example, U.S. Pat. Nos. 4,882,127; 4,849,077; 7,556,922; 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure & Ji, *Nat Biotechnol.*, 26(10):1135-45. 2008; Pihlak et al., *Nat Biotechnol.*, 26(6):676-684, 2008; Fuller et al., *Nature Biotechnol.*, 27(11):1013-1023, 2009; Mardis, *Genome Med.*, 1 (4): 40, 2009; Metzker, *Nature Rev. Genet.*, 11 (1): 31-46, 2010.

When expression of the marker is measured at the protein level, it is possible to use specific antibodies, in particular in well-known technologies such as immunoprecipitation, immunohistology, Western blot, dot blot, ELISA or ELISPOT, protein chips, antibody chips, or tissue chips coupled with immunohistochemistry. Other techniques that may be used include FRET or BRET techniques, methods of microscopy or histochemistry, notably including methods of confocal microscopy and electron microscopy, methods based on the use of one or more excitation wavelengths and a suitable optical method, such as an electrochemical method (voltammetry and amperometry techniques), atomic force microscopy, and radio frequency methods, such as multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, etc.), flow cytometry, radioisotope or magnetic resonance imaging, analysis by polyacrylamide gel electrophoresis (SDS-PAGE), HPLC-mass spectrometry and liquid chromatography-mass spectrophotometry/mass spectrometry (LC-MS/MS). All these techniques are well-known to a person skilled in the art and it is not necessary to detail them herein.

If the biological marker is a lipid, notably a ceramide, a person skilled in the art will be able to use all methods at his disposal for measuring the lipid content in a skin cell sample. These methods include, among others, high-performance liquid chromatography (HPLC, see, for example, Sullivan et al., *Arch Ophthalmol.*, 120(12):1689-99, 2002), for example coupled to an evaporative light-scattering detector (HPLC-ELSD, see Nordbäck et al., *J. High Resolut. Chromatogr.*, 22:483-486, 1999; Torres et al., *J. Chromatogr. A.*, 1078:28-34, 2005); thin-layer chromatography (TLC, for example Downing et al., *J Invest Dermatol.*, 77(4):358-360, 1981; Nordstrom et al., *J Invest Dermatol.*, 87(2):260-263, 1986); nuclear magnetic resonance (NMR, see, for example, Robosky et al., *J Lipid Res.*, 49(3):686-692, 2008); in vivo confocal Raman microspectroscopy; mass spectrometry, gas chromatography coupled to mass spectrometry (GC-MS, see O'Neill et al., *J Chromatogr Sci.*, 14(1):28-36, 1976); liquid chromatography coupled to mass spectrometry (see, for example, van Smeden et al., *J Lipid Res*, 52(6):1211-1221, 2011); ultra-performance liquid chromatography (UPLC, see Rainville et al., *J Proteome Res.*, 6(2):552-558, 2007; Castro-Perez et al., *J Proteome Res.*, 10(9):4281-4290, 2011). The organization of these lipids in the skin and, more particularly, in the stratum corneum (or corneal layer), lamellar or lateral organization, can also be analysed, for example, by x-ray diffraction (Bouwstra et al., *J Invest Dermatol.*, 97(6):1005-1012, 1991; van Smeden et al., *J Lipid Res.*, 52(6):1211-1221, 1991) or by Fourier-transform infrared spectroscopy (Gorcea et al., *Int J Pharm.* Nov. 10, 2011) or by morphometric analysis using electron microscopy (Daehnhardt-Pfeiffer et al., *Skin Pharmacol Physiol.*, 25(3):155-161, 2012) or by electron microscopy analysis of vitreous skin section combined with molecular analysis (Iwai et al., *J Invest Dermatol.*, Apr. 26, 2012).

Measurement of NMF concentration is a procedure well-known to a person skilled in the art. In particular, it is possible to measure NMF using in vivo confocal Raman microspectroscopy. This procedure has been commonly used in the field for at least 15 years. By way of example, mention may be made of, among others, the publications by Caspers et al. (*J Invest Dermatol.*, 116(3):434-442, 2001), Vyumvuhore et al. (*J Biomed Opt.*, 19(11):111603, 2014), or Falcone et al. (*Skin Pharmacol Physiol*, 28:307-317, 2015). It is also possible to measure NMFs by liquid chromatography coupled to mass spectrometry. Refer, for example, to Piraud et al. (*Rapid Commun Mass Spectrom*, 19(12):1587-602, 2005), Petritis et al. (*Journal of Chromatography A*, 833(2):147-155, 1999), Henriksen et al. (*J Am Soc Mass Spectrom*, 16(4):446-455, 2005) or Yang (Application of biophysics and bioengineering to the assessment of skin barrier function. Thesis (Doctor of Philosophy (PhD)). University of Bath, U. K., 2011).

The expression "a reference expression level of a biological marker", in the meaning of the present application, refers to any expression level of said marker used as a reference. For example, a reference expression level may be obtained by measuring the expression level of the marker of interest in a children's skin model, under particular conditions. A person skilled in the art will be able to choose these particular conditions as a function of intended purpose when implementing the invention.

According to another embodiment, the reference expression level of a biological marker is the expression level of said marker obtained in a children's skin model, contacted with a reference formulation or active agent, and exposed to drying conditions.

When the reference expression level is an expression level obtained in a skin model exposed to drying conditions, a person skilled in the art will easily understand that the drying conditions of the skin model used in the method of the invention and of the model used to obtain a reference expression level are preferentially the same. Therefore, preferentially, the drying conditions used, notably the relative humidity in the atmosphere, as well as the exposure time used in the method of the invention and in the model used to obtain a reference expression level, are preferentially the same.

For example, a person skilled in the art can use as a reference formulation any formulation known in the prior art for its effect in preventing or treating dry skin.

Preferentially, the reference formulation is an oil-in-water emulsion, such as those described below. More preferentially, the reference formulation is formulation A, which contains avocado perseoses. These are C7 sugars obtained from avocado. Avocado perseoses and their extraction methods are described in, among others, WO 2004/112742, WO 2005/105123, WO 2005/115421, WO 2008/025847, WO 2011/073281, WO 2014/017049, WO 2014/122326, WO 2015/044230, etc.

| PRODUCT A: COLD CREAM-TYPE W/O EMULSION | |
|---|---|
| RAW MATERIAL | % |
| AQUA | QS |
| CAPRYLIC/CAPRIC TRIGLYCERIDE | 5 to 20% |
| COCO-CAPRYLATE/CAPRATE | 1 to 10% |
| POLYGLYCERYL-2-DIPOLYHYDROXYSTEARATE | 1 to 10% |
| GLYCERINE | 1 to 10% |
| WAXES | 1 to 10% |
| VEGETABLE OIL | 1 to 10% |
| POLYGLYCERYL-3 DIISOSTEARATE | 1 to 5% |
| MAGNESIUM SULPHATE | 0 to 2% |
| STEARALKONIUM HECTORITE | 0 to 2% |
| PRESERVATIVES | 0 to 2% |
| *PERSEA GRATISSIMA* FRUIT EXTRACT/AVOCADO PERSEOSE | 0 to 5% |
| CERAMIDES | 0 to 1% |

| PRODUCT B: COLD CREAM-TYPE W/O EMULSION | |
|---|---|
| RAW MATERIAL | % |
| AQUA | QS |
| Paraffin oil | 1 to 10% |
| Glyceryl Stearate | 1 to 10% |
| Glycerine | 1 to 10% |
| Stearic acid | 1 to 10% |
| Cetyl alcohol | 1 to 5% |
| PEG-12 | 1 to 5% |
| Triglycerides | 1 to 5% |
| Vegetable oils | 1 to 5% |
| Vegetable waxes | 1 to 5% |
| Octyl palmitate | 0.5 to 5 |
| Carbomer | 0.5 to 2 |
| Silicones | 1 to 5% |
| Fragrance | 0.5 to 2% |
| PRESERVATIVES | 0 to 2% |
| ACTIVE AGENTS | 0 to 5% |

| PRODUCT C: COLD CREAM-TYPE W/O EMULSION | |
|---|---|
| RAW MATERIAL | % |
| AQUA | QS |
| Spring water | 5 to 10% |
| Paraffin oil | 1 to 10% |
| Cetyl palmitate | 1 to 10% |
| Glycerine | 1 to 10% |
| Glycols | 1 to 10% |
| Mineral waxes | 1 to 10% |
| Mineral oils | 1 to 10% |
| Vegetable waxes | 1 to 5% |
| MAGNESIUM SULPHATE | 0 to 2% |
| Magnesium stearate | 0 to 2% |
| Sorbitan isostearate | 1 to 5% |
| Polyglyceryl-3 polyricinoleate | 0.5 to 3% |
| PEG-30 dipolyhydroxystearate | 0.5 to 3% |
| Silicones | 0.5 to 2% |
| PRESERVATIVES | 0 to 2% |
| ACTIVE AGENTS | 0 to 5% |

| PRODUCT D: COLD CREAM-TYPE W/O EMULSION | |
|---|---|
| RAW MATERIAL | % |
| AQUA | QS |
| Spring water | 5 to 10% |
| Paraffin oil | 1 to 10% |
| Glyceryl Stearate | 1 to 10% |
| Cetyl alcohol | 1 to 10% |
| Mineral waxes | 1 to 10% |
| C-20-40 Pareth 10 | 0.5 to 5% |
| Cetyl phosphate | 0.5 to 5% |
| Fragrance | 0.5 to 2% |
| PRESERVATIVES | 0 to 2% |
| ACTIVE AGENTS | 0 to 5% |

| PRODUCT E: COLD CREAM LOTION | |
|---|---|
| INCI EU | % INCI |
| AQUA | QS |
| CAPRYLIC/CAPRIC TRIGLYCERIDE | 5 to 15% |
| GLYCERINE | 2 to 5% |
| *HELIANTHUS ANNUUS* SEED OIL | 2 to 5% |
| HYDROGENATED COCONUT OIL | 2 to 5% |
| GLYCERYL STEARATE | 1 to 3% |
| CERA ALBA | 1 to 3% |
| 1,2-HEXANEDIOL | 0.5 to 1.5% |
| CETEARETH-20 | 0.5 to 1.5% |
| FRAGRANCE | 0.5 to 1.5% |
| GLYCERYL CAPRYLATE | 0.1 to 0.5% |
| ACRYLATES/C10-30 ALKYL ACRYLATE CROSSPOLYMER | 0.1 to 0.5% |
| CETEARETH-12 | 0.1 to 0.5% |
| CETEARYL ALCOHOL | 0.1 to 0.5% |
| TOCOPHERYL ACETATE | 0.1 to 0.5% |
| SODIUM HYDROXIDE | 0.05 to 0.3% |
| *PERSEA GRATISSIMA* FRUIT EXTRACT | 0.05 to 0.3% |
| CERAMIDE NP | 0.05 to 0.3% |
| PHYTOSPHINGOSINE | 0.05 to 0.3% |
| | 100.000000 |

| Product F: Cold cream cleansing gel | |
|---|---|
| INCI EU | % INCI |
| AQUA | QS |
| GLYCERINE | 2 to 7% |

-continued

Product F: Cold cream cleansing gel

| INCI EU | % INCI |
|---|---|
| COCAMIDOPROPYL BETAINE | 1 to 5% |
| SODIUM MYRETH SULPHATE | 1 to 5% |
| COCO-GLUCOSIDE | 1 to 5% |
| PEG-3 DISTEARATE | 0.5 to 2% |
| PEG-150 DISTEARATE | 0.5 to 2% |
| GLYCERYL CAPRYLATE | 0.5 to 2% |
| GLYCOL DISTEARATE | 0.5 to 2% |
| FRAGRANCE | 0.5 to 2% |
| POLYQUATERNIUM-10 | 0.1 to 1% |
| CERA ALBA | 0.1 to 1% |
| *PRUNUS AMYGDALUS DULCIS* OIL | 0.1 to 1% |
| CITRIC ACID | 0.05 to 0.1% |
| CERAMIDE NP | 0.05 to 0.1% |
| *PERSEA GRATISSIMA* FRUIT EXTRACT | 0.05 to 0.1% |
|  | 100.000000 |

According to another preferred embodiment, the reference expression level of a biological marker is the expression level of said marker obtained in a skin model obtained from a skin sample from a child, wherein said model is not treated with the formulation or active agent of interest and is not exposed to drying conditions.

According to another preferred embodiment, the reference expression level of a biological marker is the expression level of said marker obtained in a skin model obtained from a skin sample from a child, wherein said model is not treated with the formulation or active agent of interest but is exposed to drying conditions.

According to another embodiment, the reference expression level of a biological marker is the expression level of said marker obtained in a skin model obtained from a skin sample from a child, treated with the formulation or active agent of interest and not exposed to drying conditions.

A person skilled in the art will further easily understand that the comparison of step d) is preferably carried out between the measurements of expression levels obtained for skin models obtained from skin samples from children, or from similar or even identical histological structures. The expression "similar histological structures", in the meaning of the present application, means that the relative proportions of cell types comprised in the compared skin models are similar. Thus, it is preferable that the relative proportions of cell types comprised in the skin model of step a) do not differ by more than 5% from the relative proportions of cell types comprised in the skin model used to obtain the reference expression level of step d). The expression "relative proportion of a cell type", in the meaning of the present application, refers to the ratio of the number of cells corresponding to this cell type to the total number of cells comprised in the skin model. Thus, for example, it is preferable that the proportion of keratinocytes relative to the total number of cells in the skin model of step a) does not differ by more than 5% from the proportion of keratinocytes relative to the total number of cells in the skin model used to obtain the reference expression level of step d). The expression "identical histological structures", in the meaning of the present application, means that the relative proportions of cell types comprised in the compared skin models are identical. In the meaning of the present invention, the relative proportions of cell types comprised in the nipple skin model of step a) are identical to the relative proportions of cell types comprised in the skin model used to obtain the reference expression level of step d) when they do not differ by more than 0.1%. Advantageously, the proportion of keratinocytes to the total number of cells in the skin model of step a) does not differ by more than 0.1% from the proportion of keratinocytes to the total number of cells in the skin model used to obtain the reference expression level of step d).

A person skilled in the art will also easily understand that the comparison of step d) is preferably carried out between the measurements of expression levels obtained for skin models which are of similar, or even identical, size, volume or weight. Thus, it is preferable that the size, the volume or the weight of the skin model of step a) does not differ by more than 5% from the size, the volume or the weight of the skin model used to obtain the reference expression level of step d). More preferentially, the size, the volume and the weight of the skin model of step a) do not differ by more than 5% from the size, the volume and the weight of the skin model used to obtain the reference expression level of step c). Even more preferentially, the size, the volume and the weight of the skin model of step a) do not differ by more than 0.1% from the size, the volume and the weight of the skin model used to obtain the reference expression level of step d).

Alternatively, if the skin models differ by more than 5% in terms of size, volume and weight, a person skilled in the art will be able to normalize the level obtained in step c) and the reference level of step d) using a normalization factor.

This normalization factor, for example, may be a directly accessible physical marker such as the mass of the cells of the sample, or the mass of a cellular component, such as the mass of cellular DNA or the mass of cellular protein.

It may also be advantageous to use as the normalization factor the expression level of a gene which is expressed at the same level in all, or nearly all, of the body's cells. In other words, according to a particular embodiment of the present invention, the expression level of a housekeeping gene is used as the normalization factor. According to another embodiment, the level obtained in step c) and the reference level of step d) are normalized using the expression level not of housekeeping genes but of the proteins they encode. A housekeeping gene is a gene expressed in all cell types which encodes a protein having a basic function necessary for survival of all cell types. A list of human housekeeping genes can be found in Eisenberg et al. (*Trends in Genet*, 19:362-365, 2003). The housekeeping genes according to the invention include for example the following genes: RPS28, GAPDH, B2M, TFRC, YWHAZ, RPL0, 18S, GUSB, UBC, TBP, GAPDH, PPIA, POLR2A, ACTB, PGK1, HPRT1, IPO8 and HMBS.

A person skilled in the art will thus be able to easily evaluate the efficacy of the formulation of interest as a function of the comparison in step d).

According to another aspect, the invention relates to a kit for implementing a method according to the invention, comprising the means necessary for measuring the expression level of at least one marker selected from lipids, NMF, skin inflammation markers, barrier function markers and markers preferentially expressed in stem cells. Preferably, the lipid is a ceramide, the barrier function marker is selected from DSG, SCEL, PADI1, CASP14, LOR, TGM1 and CLDN1, and the marker preferentially expressed in stem cells is selected from ΔNp63, KRT15, KRT19, BIRC5, and NOTCH1.

According to a particular embodiment, the kit according to the invention further comprises the means necessary for measuring the expression level of a combination of biological markers selected from the group comprising or consisting of:
- at least one skin inflammation marker and at least one barrier marker as defined above; or
- at least one skin inflammation marker and at least one marker preferentially expressed in stem cells, as defined above; or
- at least one barrier marker and at least one marker preferentially expressed in stem cells, as defined above.

In a more preferential embodiment, said combination comprises at least one skin inflammation marker and at least one barrier marker and at least one marker preferentially expressed in stem cells, as defined above.

The following examples are provided herein by way of illustration and, unless otherwise indicated, are not intended to be limited.

EXAMPLES

Example 1: Characterization of Babies' and Children's Dry Skin In Vivo

In order to characterize babies' and children's dry skin, an exploratory clinical study was carried out.

1. Materials and Methods

A clinical study with paediatric and dermatological supervision was carried out on two panels (Normal Skin panel and Dry Skin panel; classification after clinical examination by the investigator) of 40 subjects each, divided into 4 age groups:

Group 1: 1-28 days; Group 2: 3-6 months; Group 3: 1 year; Group 4: 2-4 years (Grp 1, Grp 2, Grp 3, Grp 4, respectively).

Biological specimens were collected on the subjects' forearm using swabs. The measurement of NMFs (natural moisturizing factors) and of ceramides was carried out on the collected specimens by liquid chromatography coupled to mass spectrometry (LC/MS) for the ceramides or by liquid chromatography coupled to UV detection (LC/UV) for the NMFs. Analysis of ceramides The presence of ceramides having a sphingoid base of type sphingosine [S], dihydrosphingosine [DS] and phytosphingosine [P] with an even-chain length of 16 to 22 carbon atoms was investigated by an LC/MS method.

The ceramides content was normalized to the amount of total proteins (BCA assay).
Analysis of NMF Components Filaggrin catabolites were measured by an LC/UV method for screening the two isomers (cis and trans) of urocanic acid (UCA) as well as L-pyrrolidone carboxylic acid (PCA).

The NMF content was normalized to the amount of total proteins (BCA assay).

2. Results and Conclusion

Figure 1:
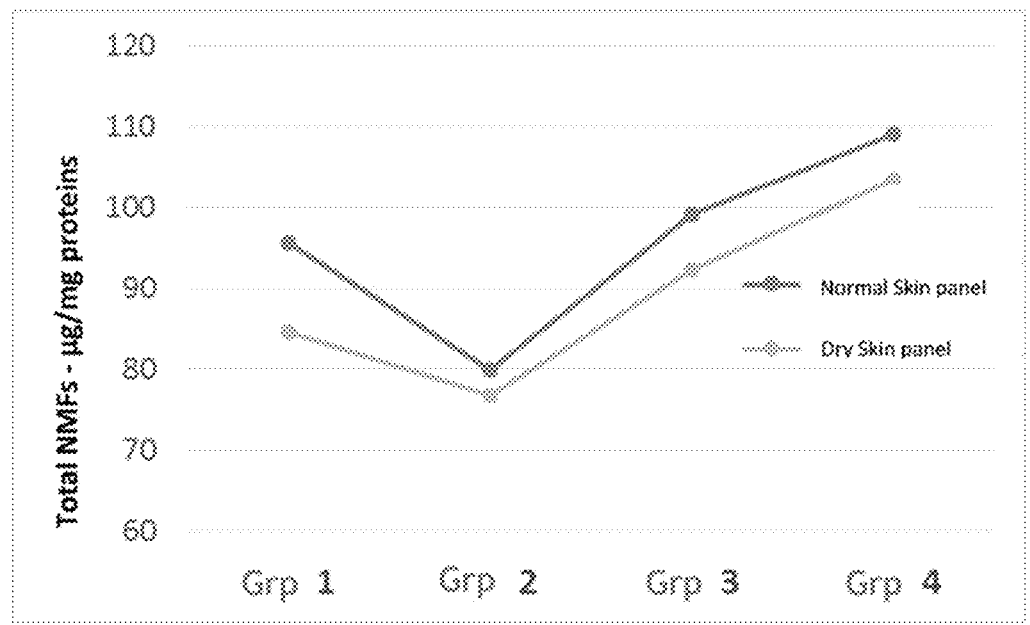
FIG. 1 shows the quantification of NMFs in the Normal Skin and Dry Skin panels, as well as the change in the amounts of NMFs as a function of age group.

The results presented below show that the subjects of the Dry Skin panel have significantly lower amounts of NMFs than those of the Normal Skin panel, regardless of age group (FIG. 1, Table 1). These observations show that low levels of NMFs constitute a biological marker of dry skin in newborns, infants and young children.

Figure 2:
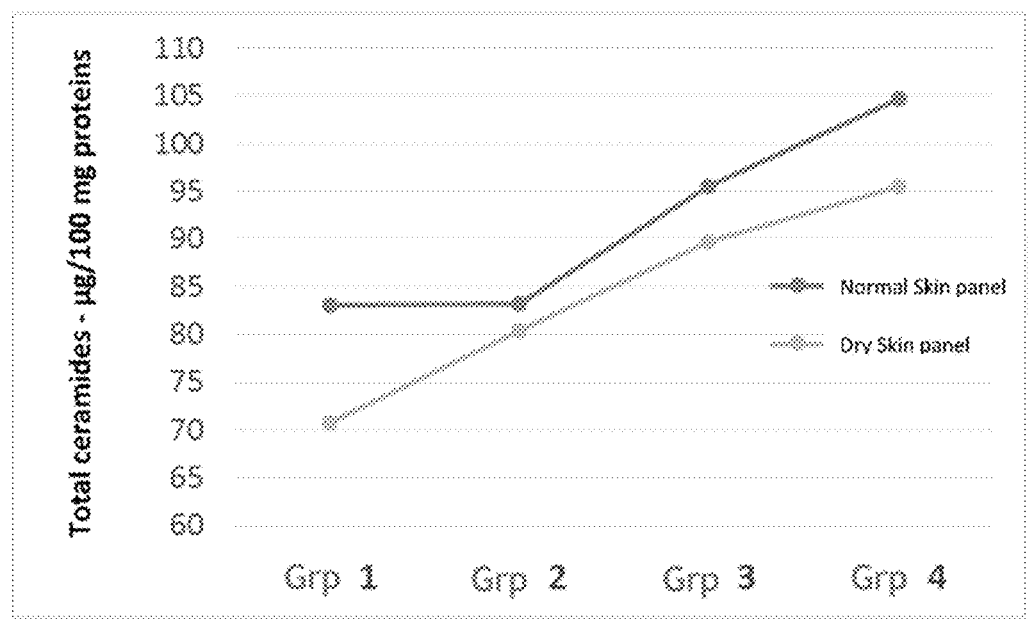
FIG. 2 shows the quantification of ceramides in the Normal Skin and Dry Skin panels, as well as the change in the amounts of ceramides as a function of age group.

Furthermore, the amounts of ceramides are lower for the subjects of the Dry Skin panel than for the subjects of the Normal Skin panel (FIG. 2, Table 1), showing that ceramides also constitute a marker of the dry skin condition in newborns, infants, and children with clinically dry skin.

In conclusion, the amount of NMFs and of ceramides is lower in children's dry skin compared with children's normal skin.

TABLE 1

Total content of NMFs and ceramides for all Normal Skin and Dry Skin panels - Student's t-test

| | Normal Skin | Dry Skin | Comparison of Dry Skin vs Normal Skin |
|---|---|---|---|
| Total NMFs (µg/mg proteins) | 97.37 | 89.43 | −8.2% p < 0.05 |
| Total ceramides (µg/100 mg proteins) | 92.68 | 84.44 | −8.9% p < 0.05 |

Example 2: Validation of the In Vitro "Dry Skin" Model

In order to validate the modelling of a dry skin phenotype, the production of NMF (natural moisturizing factor) and of ceramides by epidermises incubated in dry atmosphere was evaluated.

1. Materials and Methods

Reconstructed epidermises were prepared with keratinocytes from a donor aged 1 year.

Reconstruction of the epidermises was carried out according to a model derived from the method of Poumay et al. (*Arch Dermatol Res* 2004; 296:203-11). After 2 days of immersion culture, the reconstructed human epidermises (RHE) were grown at the air/liquid interface for 11 days.

On day 11, the epidermises were incubated for 48 h in a humid incubator for the control epidermises (normal condition: 37° C., 5% $CO_2$ and >99% relative humidity) or in a dry incubator (37° C., 5% $CO_2$ and <25% relative humidity).

At the end of incubation, the amounts of NMF and of ceramides produced by the epidermises were evaluated.

The experiments were repeated 3 times; for each these 3 tests, 3 replicates were prepared and analysed.
Analysis of Ceramides The epidermal lipids were extracted by shaking the epidermises from a mixture of organic solvents for 2 h at room temperature. Solid/liquid extraction was then carried out to isolate the ceramides from the other constitutive epidermal lipids.

The ceramide contents were analysed by LC/MS as described in Example 1.
Analysis of NMF Components The reconstructed epidermises were extracted under shaking for 2 h at room temperature from an aqueous mixture in the presence of a non-ionic surfactant to promote extraction of the markers of interest.

The NMF contents were analysed by LC/UV as described in Example 1.

2. Results and Conclusion

Ceramides are important structural components of the epidermis. They are one of the constituents of the lipid matrix of the stratum corneum. The role of this matrix is essential in the regulation of water permeability. It indeed constitutes a hydrophobic barrier which regulates water circulation through the SC. The lipid matrix is composed of an equimolar mixture of ceramides (45 to 50% of the total weight), of cholesterol (20-25%) and of free fatty acids (10-15%). Ceramides derive from the transformation of sphingomyelin by sphingomyelinases and of glucoceramides by β-glucocerebrosidase.

The major function of NMF is to maintain an optimal level of water in the stratum corneum. A well-known source of NMF constituents is filaggrin.

Incubation of the 1-year-old reconstructed epidermises in a dry incubator induced significant inhibition of the ceramide and NMF content in the epidermises (Table 2).

The decreased amount of NMF and of ceramides is one of the main features of dry skin, known and described in the literature. Moreover, Example 1 shows that the amount of NMF and of ceramides also decreases in children's dry skin. The model prepared consisting of incubation of reconstructed epidermises in dry atmosphere is thus well representative of the children's dry skin phenotype observed in vivo.

TABLE 2

NMF and ceramide content in 1-year-old reconstructed epidermises incubated under normal conditions (control) in a dry incubator (dry atmosphere)

|  | Control epidermises | Epidermises in dry atmosphere | Inhibition | Significance (Student's t-test) |
| --- | --- | --- | --- | --- |
| NMF content (µg/mg proteins) | 17.05 ± 0.21 | 12.44 ± 0.82 | −27% | P < 0.001 |
| Ceramide content (AU/mg proteins) | 173.6 ± 3.86 | 149.4 ± 2.62 | −14% | P < 0.001 |

Example 3: Evaluation of the Effect of Delipidation on the Amount of Ceramides in Reconstructed Epidermises In order to determine if other in vitro dry skin models made it possible reproduce the children's dry skin phenotype, the model of induction of dry skin by delipidation was tested. The amount of ceramides, one of the specific markers of children's dry skin, was analysed in this model.

Reconstructed epidermises were prepared according to a model derived from the method of Poumay et al. (Arch Dermatol Res 2004; 296:203-11). After 2 days of immersion culture, the reconstructed human epidermises (RHE) were grown at the air/liquid interface for 10 days.

On day 10, the epidermises were treated by topical application of a 30% 1:1 ether/acetone mixture in order to induce alteration of the barrier by delipidation, then incubated for 48 h (Miyamoto et al., 2002; Akiyama et al., 2010; Valvetcha et al., 2015).

At the end of incubation, the amounts of ceramides produced by the epidermises were evaluated.

Analysis of Ceramides

The epidermal lipids were extracted by shaking the epidermises from a mixture of organic solvents for 2 h at room temperature. Solid/liquid extraction was then carried out to isolate the ceramides from the other constitutive epidermal lipids.

The presence of ceramides having a sphingoid base of type sphingosine [S], dihydrosphingosine [DS] and phytosphingosine [P] with an even-chain length of 16 to 22 carbon atoms was investigated by an LC/MS method.

Results and Conclusion

Delipidation of the epidermises by ether/acetone treatment does not induce a decrease in the amount of ceramides produced by the epidermises (Table 3).

Therefore, surprisingly, delipidation does not allow modelling of the dry skin phenotype shown in vivo. Only the "dry skin" model obtained by incubation in a dry-atmosphere incubator designed by the present Inventors and described in Example 2 above makes it possible to reproduce the phenotype observed in vivo for children's dry skin.

TABLE 3

Total ceramide content for the control epidermises and the delipidated epidermises - Student's t-test

|  | Control epidermis | Delipidated epidermis | Comparison of Delipidated epidermis vs Control epidermis |
| --- | --- | --- | --- |
| Ceramides (arbitrary units) | 234.3 ± 26.0 | 227.9 ± 3.9 | −2.8% ns |

Example 4: Characterization of the Response of Infants' Epidermises Compared with Adult Epidermises 1. Materials and Methods Reconstructed epidermises were prepared, as described above, first with the keratinocytes of a 1-year-old donor and second with the keratinocytes of a 19-year-old donor; the keratinocytes of these two donors coming from a foreskin specimen.

On day 10, the epidermises were incubated for 24 h to 48 h in a humid incubator for the control epidermises (normal condition: 37° C., 5% $CO_2$ and >99% relative humidity) or in a dry incubator (37° C., 5% $CO_2$ and <25% relative humidity).

After 24 h of incubation, the gene expression of inflammation, hydration, barrier function and stem cell markers was evaluated by real-time quantitative PCR (qRT-PCR).

After 48 h of incubation, the viability and the morphology of the epidermises were studied.

Evaluation of the Viability of the Reconstructed Epidermises

The viability of the epidermises was evaluated by an MTT reduction test (n=2): the epidermises were incubated in the presence of MTT (tetrazolium salt), the transformation of which into blue formazan crystals is proportional to succinate dehydrogenase (mitochondrial enzyme) activity. After dissociation of the cells and solubilization of the formazan by addition of isopropanol/HCl, the optical density (OD), representative of the number of living cells and their metabolic activity, was measured at 540 nm.

Evaluation of the Morphology of the Reconstructed Epidermises

The morphology of the reconstructed epidermises was evaluated (n=2) by histological analysis after haematoxylin/eosin staining.

The epidermises were fixed and imbedded in paraffin, cross-sections were prepared with a microtome. The sections were deparaffinized and then stained with haematoxylin/eosin. Haematoxylin stains the cell nuclei blue/purple; eosin stains the cytoplasms varying intensities of pink.

Microscopic analysis of the histological sections made it possible to evaluate and to quantify certain morphological parameters such as the thickness of the layer of living cells.

Differential Gene Expression Analysis

Expression of the markers was evaluated by qRT-PCR on messenger RNA extracted from the RHE of each treatment.

The gene expression analysis was carried out (n=2) using a PCR array containing 30 genes of interest and 2 reference genes (housekeeping genes). Total RNA from each sample was extracted using TriPure Isolation Reagent® according to the protocol recommended by the supplier. The amount and the quality of the RNA were evaluated by capillary electrophoresis (Bioanalyzer, Agilent). Complementary DNA (cDNA) was synthesized by reverse transcription of RNA in the presence of oligo(dT) and "Transcriptor Reverse Transcriptase" enzyme. The cDNA obtained was quantified by spectrophotometry and then the amounts of cDNA were adjusted.

The PCR reactions were performed by quantitative PCR with the "LightCycler" system (Roche Molecular Systems Inc.) and according to the procedure recommended by the supplier. The reaction mixture for each sample was: cDNA, primers for the various markers used, reaction mixture containing Taq DNA polymerase enzyme, SYBR Green I marker (DNA intercalating agent) and $MgCl_2$.

Fluorescence incorporation in the amplified DNA is measured continuously during the PCR cycles.

Quantitative analysis of the results is based on the collection of threshold cycles (Ct). The threshold cycle is the point at which the fluorescence emission signal is statistically and significantly higher than the background. The threshold cycle is directly correlated with the initial copy number of target DNA.

Table 4 lists the genes studied.

The relative gene expression value (RE) is expressed in arbitrary units according to the following formula:

$$RE = (\tfrac{1}{2}_{cycle\ number}) \times 10^6$$

TABLE 4

Classification and name of the genes studied

| Cluster name | Abbreviation | Gene name |
| --- | --- | --- |
| Housekeeping | RPS28 | Ribosomal protein 28S |
|  | GAPDH | Glyceraldehyde-3-phosphate dehydrogenase |
|  | IL1A | Interleukin 1 alpha |
|  | IL8 | Interleukin 8 |
| Aspecific and neurogenic inflammation | PTGS2 | Prostaglandin synthase 2 |
|  | NGFR | Nerve growth factor receptor |
|  | PLA2G2F | Phospholipase A2 group IIF |
|  | TAC1 | Tachykinin precursor 1, or substance P |
|  | TAC1R | Tachykinin receptor 1, or substance P receptor |
|  | TRPV1 | Transient receptor potential cation channel, subfamily V, member 1 |
|  | TRPV3 | Transient receptor potential cation channel, subfamily V, member 3 |
|  | MRGPRD | MAS related GPR family member D |
|  | F2RL1 | Coagulation factor II (thrombin) receptor-like 1 or proteinase activated receptor 2 (PAR2) |
|  | OSMR | Oncostatin M receptor, interleukin 31 receptor |
| Epidermal differentiation, Barrier function, Hydration | DSG | Desmoglein 1 |
|  | SCEL | Sciellin |
|  | PADI1 | Peptidylarginine deiminase 1 |

TABLE 4-continued

Classification and name of the genes studied

| Cluster name | Abbreviation | Gene name |
| --- | --- | --- |
|  | CASP14 | Caspase 14 |
|  | LOR | Loricrin |
|  | TGM1 | Transglutaminase 1 |
|  | CLDN1 | Claudin 1 |
|  | TP63 | Tumour protein P63 |
|  | KRT15 | Keratin 15 |
| Stem cells | KRT19 | Keratin 19 |
|  | BIRC5 | Baculoviral IAP repeat-containing 5 (survivin) |
|  | NOTCH1 | Notch homolog 1 |

2. Results a. Morphology and Viability of the Epidermises

Incubation in dry atmosphere did not heavily alter the morphology of the epidermises observed under the microscope after haematoxylin/eosin staining (data not shown); furthermore, the viability of the 1-year-old epidermises and of the adult epidermises was impacted in the same manner (30% and 29% inhibition, respectively, Table 5). However, the measurement of the thickness of the layer of living cells was more heavily impacted in the 1-year-old epidermises (−18%) compared with the adult epidermises in which no decrease in this parameter is observed (Table 5).

These observations tend to show an increased sensitivity of the 1-year-old epidermises to dehydration stress.

TABLE 5

Analysis of the viability and the thickness of the layer of living cells

|  | Viability (MTT) | Control | Dry atmosphere |
| --- | --- | --- | --- |
| Viability (MTT) | 1-year-old | 100% | 70% |
|  | Adult | 100% | 71% |
| Thickness of the layer of living cells | 1-year-old | 100% | 82% |
|  | Adult | 100% | 100% | b. Analysis of Expression of Gene Markers of Aspecific and Neurogenic Inflammation Incubation in dry atmosphere induced an increase in the expression level of markers of aspecific and neurogenic inflammation, both in the 1-year-old reconstructed epidermises and in the adult reconstructed epidermises (Table 6).

However, this stimulation is much greater in the case of infants' reconstructed epidermises (+355%) compared with adult epidermises (+114%).

This suggests an increased sensitivity of infants' epidermises, the inflammatory and neurosensory response of which is exacerbated in response to dehydration stress.

TABLE 6

Level of gene expression of inflammation markers (relative expression in % compared with the control grown under normal conditions)

|  | Control 1-year-old epidermises | 1-year-old epidermises in dry atmosphere | Control adult epidermises | Adult epidermises in dry atmosphere |
| --- | --- | --- | --- | --- |
| IL1A | 100 | 177 | 100 | 155 |
| IL8 | 100 | 314 | 100 | 147 |
| PTGS2 | 100 | 1421 | 100 | 666 |
| NGFR | 100 | 223 | 100 | 100 |
| TRPV1 | 100 | 675.5 | 100 | 125 |

TABLE 6-continued

Level of gene expression of inflammation markers (relative expression in % compared with the control grown under normal conditions)

| | Control 1-year-old epidermises | 1-year-old epidermises in dry atmosphere | Control adult epidermises | Adult epidermises in dry atmosphere |
|---|---|---|---|---|
| TRPV3 | 100 | 606 | 100 | 150 |
| MRGPRD | 100 | 246 | 100 | 351 |
| F2RL1 | 100 | 171 | 100 | 119 |
| OSMR | 100 | 263 | 100 | 113 |
| Mean expression of inflammation markers (%) | 100 | 455 | 100 | 214 |
| Increase relative to the control (%) | — | 355% | — | 114% | c. Analysis of Expression of Stem Cell Marker Genes

The stem cells of tissues undergoing permanent renewal are traditionally defined as being rare and relatively quiescent cells. They have a unique capacity of self-renewal and of tissue regeneration which enables them to provide homeostasis and integrity to the tissue in which they reside.

Among the epidermal stem cells, the interfollicular stem cells located in the basal layer constitute the chief epidermal stem cell reservoir. These cells reside in an anatomical and functional microenvironment, the niche, which helps maintain their characteristics, notably when the physiological conditions change. Interfollicular stem cells and their niches are involved in maintaining skin integrity and regeneration. Stem cells are identifiable only by following several markers. We thus evaluated the expression level of various gene markers characteristic of stem cells in the "dry skin" model.

Incubation in dry atmosphere induced a substantial decrease (−45%) in the mean expression level of the stem cell marker pool studied (Table 7) in the 1-year-old epidermises, whereas no inhibition of expression of these markers was observed in the adult epidermises (+12%).

This tends to show an increased vulnerability of this cell capital in the 1-year-old epidermises.

TABLE 7

Expression level of stem cell marker genes (relative expression in % compared with the 1-year-old control)

| | Control 1-year-old epidermises | 1-year-old epidermises in dry atmosphere | Control adult epidermises | Adult epidermises in dry atmosphere |
|---|---|---|---|---|
| KRT19 | 100 | 65 | 84 | 120 |
| BIRC5 | 100 | 64 | 85 | 94 |
| TP63 | 100 | 13 | 86 | 80 |
| NOTCH1 | 100 | 77 | 45 | 43 |
| Mean expression of the stem cell marker pool (%) | 100 | 55 | 75 | 84 |
| Modulation relative to the control (%) | — | −45% | — | +12% | d. Analysis of Expression of Barrier and Hydration Marker Genes

Incubation in dry atmosphere induced a decrease in the expression level of barrier markers, both in the 1-year-old reconstructed epidermises and in the adult reconstructed epidermises (Table 8).

However, this inhibition is greater in the case of infants' reconstructed epidermises (−57%) compared with adult epidermises (−38%).

This suggests a greater vulnerability of the barrier function markers in the infants' epidermises.

TABLE 8

Expression level of barrier and hydration marker genes (relative expression in % compared with the 1-year-old control)

| | Control 1-year-old epidermises | 1-year-old epidermises in dry atmosphere | Control adult epidermises | Adult epidermises in dry atmosphere |
|---|---|---|---|---|
| DSG1 | 100 | 56 | 153 | 92 |
| SCEL | 100 | 20 | 62 | 34 |
| PADI1 | 100 | 51 | 117 | 78 |
| CASP14 | 100 | 47 | 112 | 74 |
| Mean expression of barrier markers (%) | 100 | 43 | 111 | 69 |
| Inhibition relative to the control (%) | — | −57% | — | −38% |

Desmoglein 1 (DSG1) is a constitutive protein of corneodesmosomes which provides corneocyte cohesiveness within the corneal layer.

Sciellin (SCL) is a precursor of the cornified envelope.

PADI1 (peptidylarginine deiminase 1) and caspase 14 (CASP14) are two enzymes involved in the processing of filaggrin to obtain NMF.3. Conclusion Comparative analysis of the behaviour of the 1-year-old and the adult (19-year-old) reconstructed epidermises in the dry skin induction model shows a greater vulnerability and susceptibility of the infants' epidermises to dehydration stress induced by incubation in dry atmosphere.

This greater vulnerability justifies the development of cosmetic products for dry skin specifically adapted to babies' skin.

Example 5: Evaluation of Products for Dry Skin

The babies' dry skin model previously prepared, consisting in incubating 1-year-old infants' reconstructed epidermises in dry atmosphere, was used for a comparative evaluation of the biological efficacy of 4 cosmetic products for dry skin.

1. Materials and Methods

Reconstructed epidermises were prepared, as described above, from keratinocytes of a 1-year-old donor.

On day 11, the epidermises were treated by topical application of the test products in the amount of 5 mg/cm$^2$ and then incubated for 6 h, 24 h or 48 h in a dry incubator (dry atmosphere condition: 37° C., 5% $CO_2$ and <25% relative humidity), except for the control epidermises in a humid incubator (37° C., 5% $CO_2$ and >99% relative humidity) and analysed as described above:

After 6 h and 24 h of incubation, the gene expression of markers of aspecific and neurogenic inflammation, of hydration, of the barrier function and of stem cells (Table 1) was evaluated (n=2) by real-time quantitative PCR (qRT-PCR).

After 48 h of incubation, the viability (MTT) and the morphology (histology, haematoxylin/eosin staining) of the epidermises were studied (n=2) and the production of NMF and ceramides was analysed (n=3).

Test products=reference formulations as cited above:
Product A
Product B
Product C
Product D

2. Results a. Morphology and Viability of the Epidermises

Just as during the preceding model development step, incubation in dry atmosphere did not significantly alter the morphology and the viability of the epidermises (Table 9).

TABLE 9

Analysis of the viability of the epidermises

|  | Viability (MTT) |
|---|---|
| Control epidermis | 100% |
| Dry incubator control | 87% |
| Product A | 90% |
| Product B | 89% |
| Product C | 75% |
| Product D | 97% | b. Analysis of Expression of Neurogenic and Aspecific Inflammation Marker Genes Products A, B and C inhibit the inflammation markers expressed under conditions of incubation in dry atmosphere (Table 10). These products thus offer protection against the skin reactivity which can be exacerbated under these conditions. Only product D has no inhibitory effect on these markers.

TABLE 10

Level of gene expression of markers of neurogenic and aspecific inflammation (relative expression in % compared with the dry incubator control)

|  | PLA2G2F | TAC1 | TAC1R | Mean expression of markers (%) | Inhibition relative to the dry incubator control |
|---|---|---|---|---|---|
| Dry incubator control | 100 | 100 | 100 | 100 |  |
| Product A | 90.5 | 81.5 | 70 | 81 | −19% |
| Product B | 75.5 | 66 | 55 | 65 | −35% |
| Product C | 103.5 | 75.5 | 75 | 85 | −15% |
| Product D | 87.5 | 95.5 | 105.5 | 96 | −4% | c. Analysis of Expression of Stem Cell Marker Genes

Only product A fully restores (96% restoration) the expression level of stem cell markers inhibited by incubation in dry atmosphere with an efficacy superior to the other products tested (Table 11).

Product A thus protects the cell capital in the dry skin model.

TABLE 11

Expression level of stem cells marker genes (relative expression in % compared with the 1-year-old control)

|  | KRT15 | KRT19 | BIRC5 | TP63 | Mean expression of the stem cell marker pool (%) | % restoration |
|---|---|---|---|---|---|---|
| Control | 100 | 100 | 100 | 100 | 100 |  |
| Dry incubator control | 25 | 74 | 45 | 47 | 48 |  |
| Product A | 97 | 130 | 78 | 90 | 98 | 96% |
| Product B | 80 | 68 | 32 | 62 | 61 | 61% |
| Product C | 86 | 131 | 21 | 70 | 77 | 77% |
| Product D | 86 | 74 | 19 | 71 | 63 | 63% | d. Analysis of Expression of Barrier Marker Genes

Under conditions of incubation in dry atmosphere, products A and B restored the expression level of barrier marker genes and show a restoration efficacy (140% and 113%, respectively) superior to the other formulas tested (Table 12).

Therefore, product A, and to a lesser extent product B, protect the expression of barrier markers altered by incubation in dry atmosphere.

TABLE 12

Expression level of barrier marker genes (relative expression in % compared with the 1-year-old control)

|  | LOR | TGM1 | CLDN1 | DSG1 | Mean expression of barrier markers (%) | % restoration |
|---|---|---|---|---|---|---|
| Control | 100 | 100 | 100 | 100 | 100 |  |
| Dry incubator control | 88 | 93 | 93 | 68 | 85 |  |
| Product A | 103 | 109 | 111 | 103 | 106 | 140 |
| Product B | 97 | 109 | 110 | 91 | 102 | 113 |
| Product C | 78 | 91 | 92 | 114 | 94 | 60 |
| Product D | 72 | 87 | 86 | 101 | 87 | 13 |

Loricrin (LOR) is a late marker of epidermal differentiation involved in formation of the cornified envelope.
Transglutaminase 1 (TGM1) is an enzyme responsible for cross-linking various proteins during production of the cornified envelope, ensuring the impermeability/solidity of the stratum corneum.
Claudin 1 (CLDN1) is one of the constitutive proteins of tight junctions, involved in the skin barrier function, notably controlling water flow.
Desmoglein 1 (DSG1) is a constitutive protein of corneodesmosomes which provides corneocyte cohesiveness within the corneal layer.
Corneodesmosin is a constitutive protein of corneodesmosomes, junctions which form between corneocytes to maintain the structure of the stratum corneum and thus to take part in proper desquamation of the skin [10].

e. Analysis of NMF and Ceramide Production

Products A and B made it possible to restore the ceramide and NMF production inhibited in the dry skin model (Table 13) whereas the two other products tested (C and D) show lesser efficacy: practically no effect on ceramide production, a small increase in NMF production.

TABLE 13

NMF and ceramide content in 1-year-old reconstructed epidermises incubated under normal conditions (control) in a dry incubator (dry atmosphere)

|  | NMF content (μg/mg proteins) |  | Ceramide content (AU/mg proteins) |  |
|---|---|---|---|---|
| Control | 16.6 ± 1.8 |  | 179.5 |  |
| Dry incubator control | 11.7 ± 8.8 | −30% | 138.25 | −23% |
| Product A | 17.3 ± 3.6 | +48% | 178.25 | +24% |
| Product B | 18.3 ± 8.1 | +56% | 183.25 | +27% |
| Product C | 13.9 ± 2 | +19% | 127.3 | −12% |
| Product D | 14.5 ± 1.7 | +24% | 150.95 | +5% |

The invention claimed is:

1. A method for evaluating the in vitro efficacy of an active agent or of a formulation in reducing the effects of dehydration on children's skin, characterized by said method comprising the following steps:
 a. incubating a reconstructed skin model under drying conditions, wherein the drying conditions comprises a relative humidity in the atmosphere of 25% or less;
 b. contacting said active agent or said formulation with the reconstructed skin model of step a;
 c. measuring the expression level of a combination of biological markers in the skin model of step b, wherein the biological markers comprise inflammation markers IL1A, IL8, PTGS2, NGFR, TAC1, TAC1R, TRPV1, TRPV3, MRGPRD, OSMR, PLA2G2F, and F2RL1; barrier function markers DSG, SCEL, POADI1, CASP14, LOR, TGM1, and CLDN1; and stem cell markers Tp63, KRT15, KRT19, BIRC5, and NOTCH1;
 d. measuring the amounts of natural moisturizing factors (NMFs) and ceramides in the skin model of step b;
 e. comparing the expression levels of the biological markers and the amounts of NMFs and ceramides to a control reconstructed skin model not exposed to drying conditions, wherein both the reconstructed skin model and the control reconstructed skin model are obtained from skin samples from a donor between newborn and 2 years, and determining that the agent or formulation is able to protect against dryness when the dried reconstructed skin model exposed to the agent or formulation has:
  i. the same or a lower expression level of the following inflammation markers: IL1A, IL8, PTGS2, NGFR, TAC1, TAC1R, TRPV1, TRPV3, MRGPRD, OSMR, PLA2G2F, and F2RL1 when compared to the control reconstructed skin model;
  ii. the same or a higher expression level of the following barrier function markers: DSG, SCEL, PAD1L, CASP14, LOR, TGM1, and CLDN1 when compared to the control reconstructed skin model;
  iii. the same or a higher expression level of the following stem cell markers: Tp63, KRT15, KRT19, BIRC5, and NOTCH1 when compared to the control reconstructed skin model;
  iv. the same or a higher amount of NMFs and ceramides.

2. The method of claim 1, wherein the reconstructed skin model comes from skin having a phototype I, II, III, IV, V, or VI.

3. The method of claim 1, wherein the reconstructed skin model is selected from suspended skin cell cultures, monolayer skin cell cultures, bilayer skin cell cultures, reconstructed skin cultures, and reconstructed mucosal cultures.

4. The method of claim 1, wherein the reconstructed skin model comes from a skin tissue explant or from differentiated cells.

5. The method of claim 1, wherein the reconstructed skin model comprises at least fibroblasts and keratinocytes.

* * * * *